United States Patent [19]

Jeutter et al.

[11] Patent Number: 5,314,457
[45] Date of Patent: May 24, 1994

[54] REGENERATIVE ELECTRICAL

[76] Inventors: Dean C. Jeutter, 246 Oak St., Grafton, Wis. 53024; Mark S. Geisler, 7819 S. 83rd St., Franklin, Wis. 53132

[21] Appl. No.: 44,634

[22] Filed: Apr. 8, 1993

[51] Int. Cl.$^5$ .............................................. A61N 1/36
[52] U.S. Cl. ...................................... 607/116; 607/60; 607/65; 128/903
[58] Field of Search ...................... 607/60, 65, 116, 32, 607/30, 115; 128/903

[56] References Cited

U.S. PATENT DOCUMENTS

| | | | |
|---|---|---|---|
| Re. 32,947 | 6/1989 | Dormer et al. | 607/57 |
| 3,195,540 | 7/1965 | Waller | 607/33 |
| 4,194,179 | 3/1980 | Malinouskas | 340/870.11 |
| 4,281,664 | 8/1981 | Duggan | 128/696 |
| 4,374,382 | 2/1983 | Markowitz | 340/870.01 |
| 4,561,443 | 12/1985 | Hogrefe et al. | 607/32 |
| 4,679,560 | 7/1987 | Galbraith | 607/60 |
| 4,726,378 | 2/1988 | Kaplan | 607/115 |
| 4,741,341 | 5/1988 | Marach | 607/32 |
| 4,809,697 | 3/1989 | Causey, III et al. | 607/31 |
| 4,940,052 | 7/1990 | Mann et al. | 607/17 |
| 4,969,464 | 11/1990 | Callaghan et al. | 607/28 |
| 4,979,506 | 12/1990 | Silvian | 607/32 |
| 5,069,210 | 12/1991 | Jeutter et al. | 607/57 |

OTHER PUBLICATIONS

Allen, H., Knutti J., Meindl J., "Integrated Power Controllers and RF Transmitters", 1979.
Jeutter, D., "Principles and Applications of Biotelemetry", SPIE vol. 1355 Telecommunication for Health Care: Telemetry, Teleradiology, and Telemedicine (1990).
Geisler, M. S., "An Externally Programmable Microcontroller Based Neural Stimulator", Marquette Univ. Master's Thesis, 1984.
Jeutter, D. C., Biomedical Telemetry Techniques, CRC Critical Reviews in Biomedical Engineering: pp. 121–174, Feb. 1982.
Jeutter, D. C., "A Transcutaneous Implanted Battery Recharging and Biotelemeter Power Switching System", IEEE Trnas. Biomed. Eng., BME-29.
Jeutter, C. D., Extending Implanted Biotelemeter Lifetime by External Switching and Battery Recharging. Proceedings of the 1979 IEEE/EMBS Conference, 1:1979.
Dialog Database Search Results Dated Aug. 20, 1992.

*Primary Examiner*—William E. Kamm
*Assistant Examiner*—George Manuel

[57] ABSTRACT

A regenerative electrical stimulation device comprising a stimulator portion to be surgically implanted in patients and an external controller portion. The implanted stimulator portion provides electrical stimuli of selected parameters to damaged nerve tissue to stimulate regeneration and/or healing of the damaged nerve tissue. The external controller portion communicates with the implanted stimulator portion to turn the stimulator portion on and off, to change the parameters of the electrical stimuli, to recharge the batteries, and to monitor the status of the batteries. The implanted portion has an antenna coil, a receiver, a programmable control processor, rechargeable batteries, and a passive transmitter. The external controller portion has an antenna coil, a control processor, a transmitter, a receiver for receiving the data passively transmitted by the implantable portion, and a display means.

22 Claims, 20 Drawing Sheets

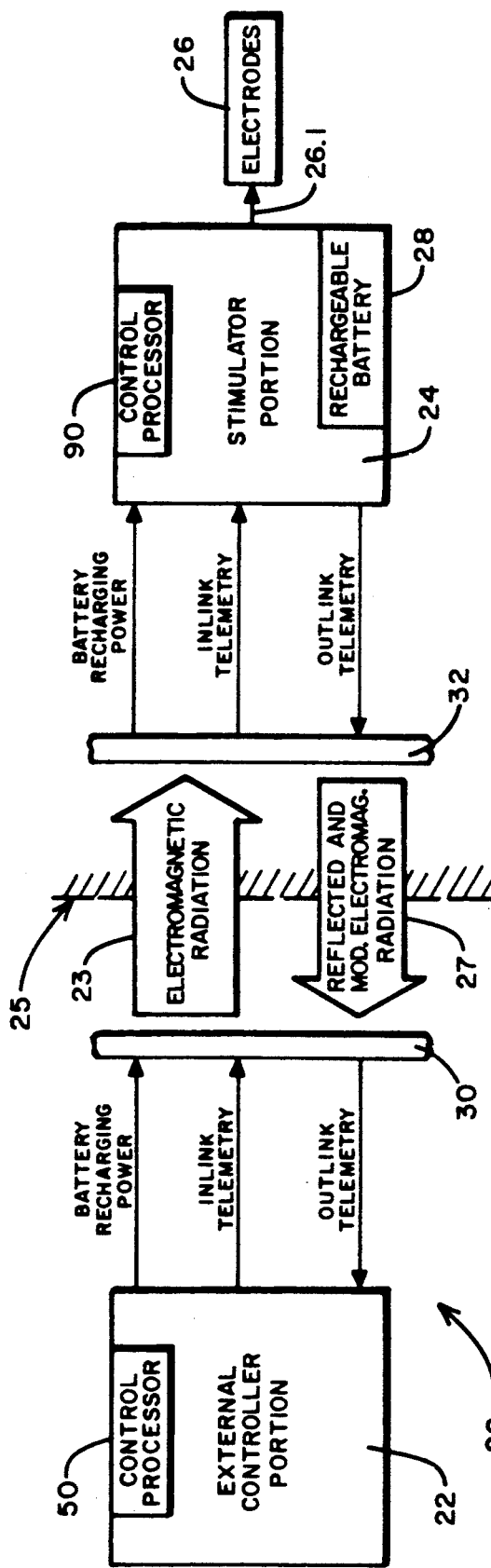
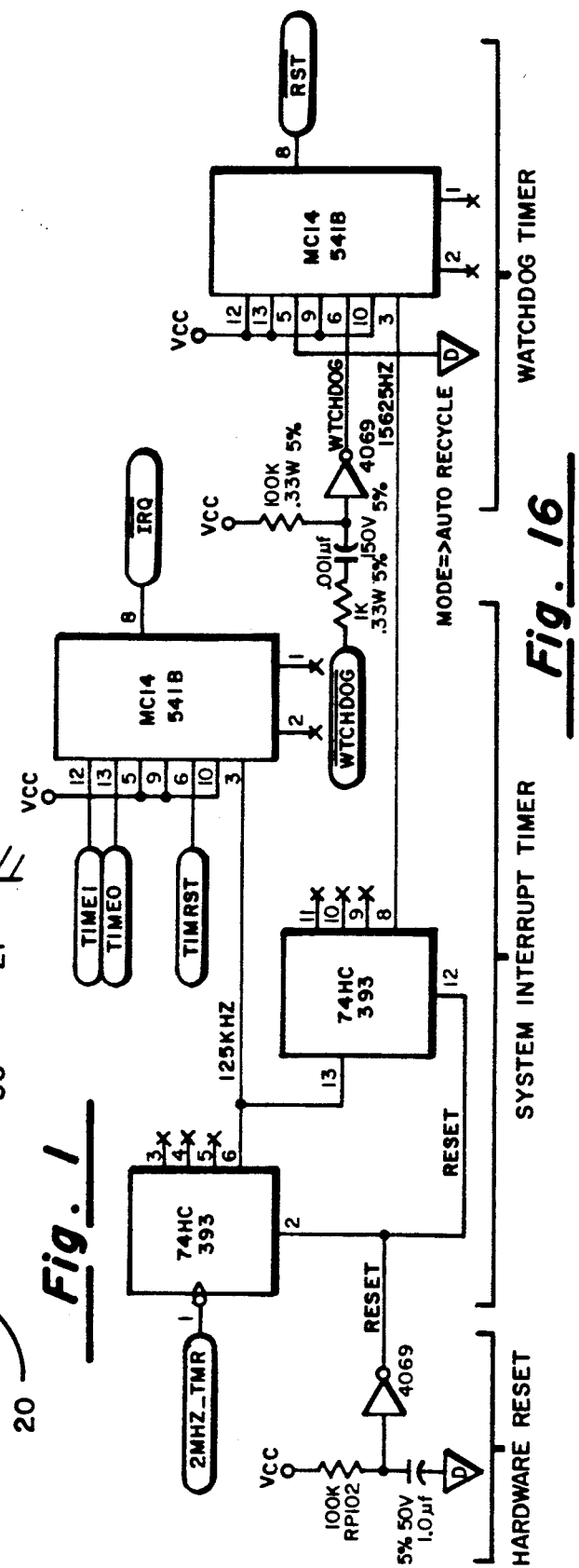
Fig. 1
Fig. 16

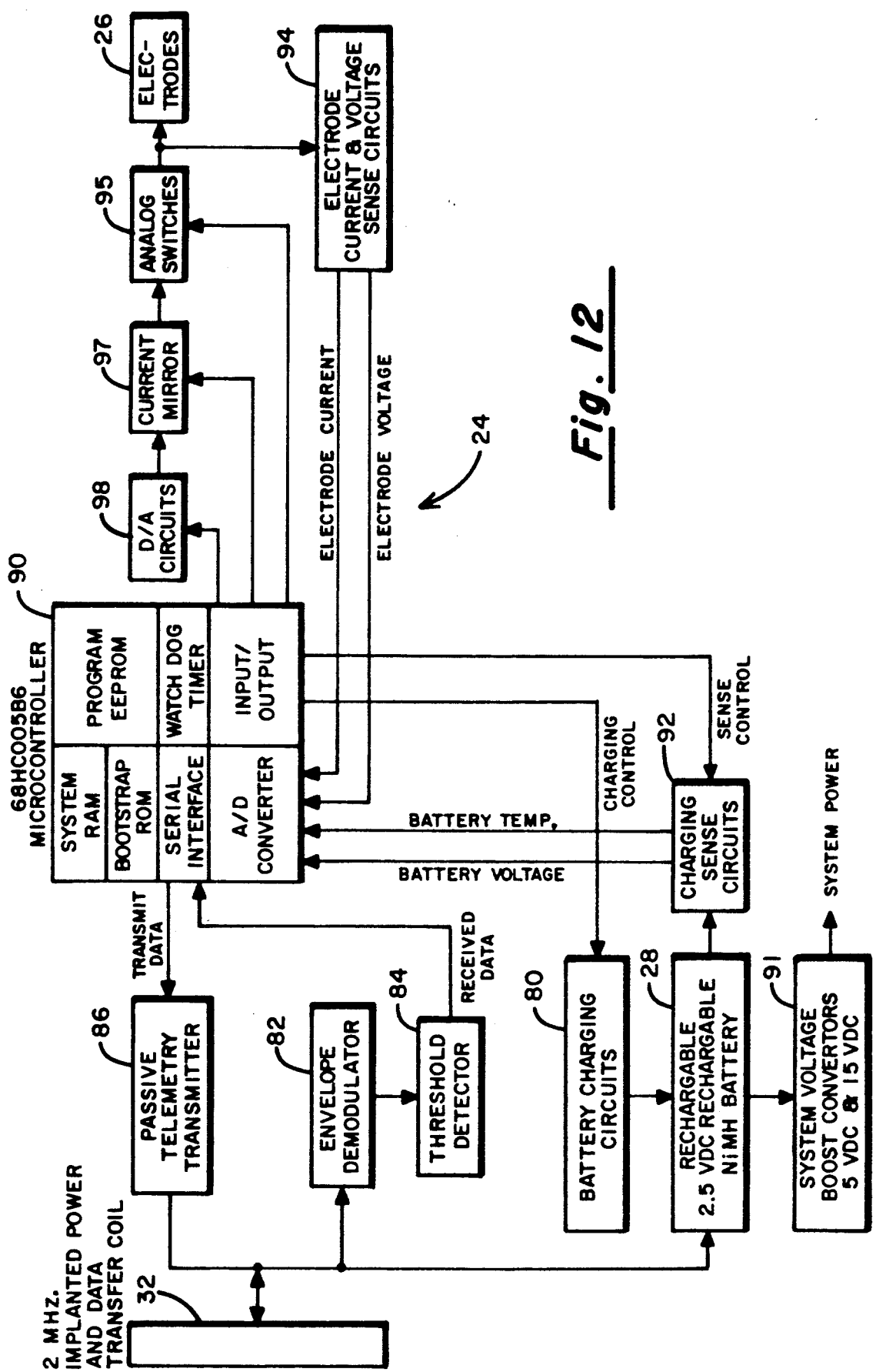

REGENERATIVE ELECTRICAL

BACKGROUND OF THE INVENTION

Electrical stimulation of damaged neural tissue as a therapeutic agent has been demonstrated to be effective to restore or improve neural function in some cases. The electrical stimulation of a patient's neural tissue is accomplished by placing electrodes in contact with or in proximity to the neural tissue and applying an electrical potential to the electrodes. This necessitates the intrusion into the patient of, at a minimum, electrodes for the stimulation. Different parameters of neural stimulation may be appropriate for different patients for different types of neural injuries, and for different stages of treatment. Additionally, the appropriate length of time over which the stimuli is to be applied may vary greatly.

To minimize the potential for infection and to allow freedom from external equipment during stimulation, an implantable stimulation device is desirable. The device should have a non-invasive battery replenishment means, should be able to alter the stimulation characteristics while implanted, and should be able to transmit pertinent data out of the body with minimal energy consumption.

SUMMARY OF THE INVENTION

A regenerative electrical stimulation device comprising a stimulator portion to be surgically implanted in patients and an external controller portion. The implanted stimulator portion provides electrical stimuli of selected parameters to damaged nerve tissue to stimulate regeneration and/or healing of the damaged nerve tissue. The external controller portion communicates with the implanted stimulator portion to turn the stimulator portion on and off, to change the parameters of the electrical stimuli, to recharge the batteries, and to monitor the status of the batteries. The implanted portion has an antenna coil, a receiver, a programmable control processor, rechargeable batteries, and a passive transmitter. The external controller portion has an antenna coil, a control processor, a transmitter, a receiver for receiving the data passively transmitted by the implantable portion, and a display means.

The external controller portion generates and emits electromagnetic energy from its antenna coil in the form of a 2 megahertz carrier wave. The external controller modulates the carrier wave for transmitting commands to the stimulator portion. The antenna coil of the stimulator portion couples with the antenna coil of the external controller to receive the electromagnetic energy. The stimulator portion rectifies the carrier wave to provide the power to recharge the rechargeable batteries and to demodulate the modulated carrier wave for receiving the commands from the controller portion. The implanted portion passively transmits information to the external controller portion by short circuiting a tuned circuit comprised of the antenna coil and a capacitor. This operates to reflect radio frequency energy back to the external control portion. The short circuit is accomplished by metal-oxide-semiconductor (MOS) field-effect transistors which switch on/off in accordance with the digital data transmitted to the external controller. The receiver has a demodulator to convert the reflected radio frequency energy into the digital data which is processed by the control processor of the external control portion and displayed if desired.

A feature of the invention is that the stimulator portion is surgically implantable providing stimulation of neural tissue with no percutaneous passage of wires, tubes or other connecting devices.

Another feature of the invention is that the device offers a wide range of flexibility with regard to parameters of the electrical stimuli presented to the electrodes. The parameters can be controlled and changed by the external controller with the stimulator portion remaining implanted.

Another feature of the invention is that the batteries of the implanted stimulator portion are rechargeable and the recharging is accomplished transcutaneously.

Another feature of the invention is that the implanted stimulator portion passively and transcutaneously transmits selected data to the external controller portion minimizing power consumption and extending the time between battery charges.

Another feature of the invention is that the implanted portion transcutaneously receives commands or transmits requested data to the external control portion while it recharges its batteries.

Another feature of the invention is that the stimulator portion utilizes the same antenna coil for the power transfer function to recharge the batteries, for receiving commands, and for passively transmitting data.

Another feature is that the external controller portion utilizes a single antenna coil for its telemetry functions and for providing the power for recharging the stimulator portion's batteries.

BRIEF DESCRIPTION OF THE DRAWINGS

FIG. 1 is a simplified block diagram of the regenerative electrical stimulator.

FIG. 12 is a block diagram of the stimulator portion.

FIG. 16 is a schematic of the system interrupt timer and watchdog timer for the stimulator portion.

DETAILED DESCRIPTION OF THE PREFERRED EMBODIMENTS

Figure 2:
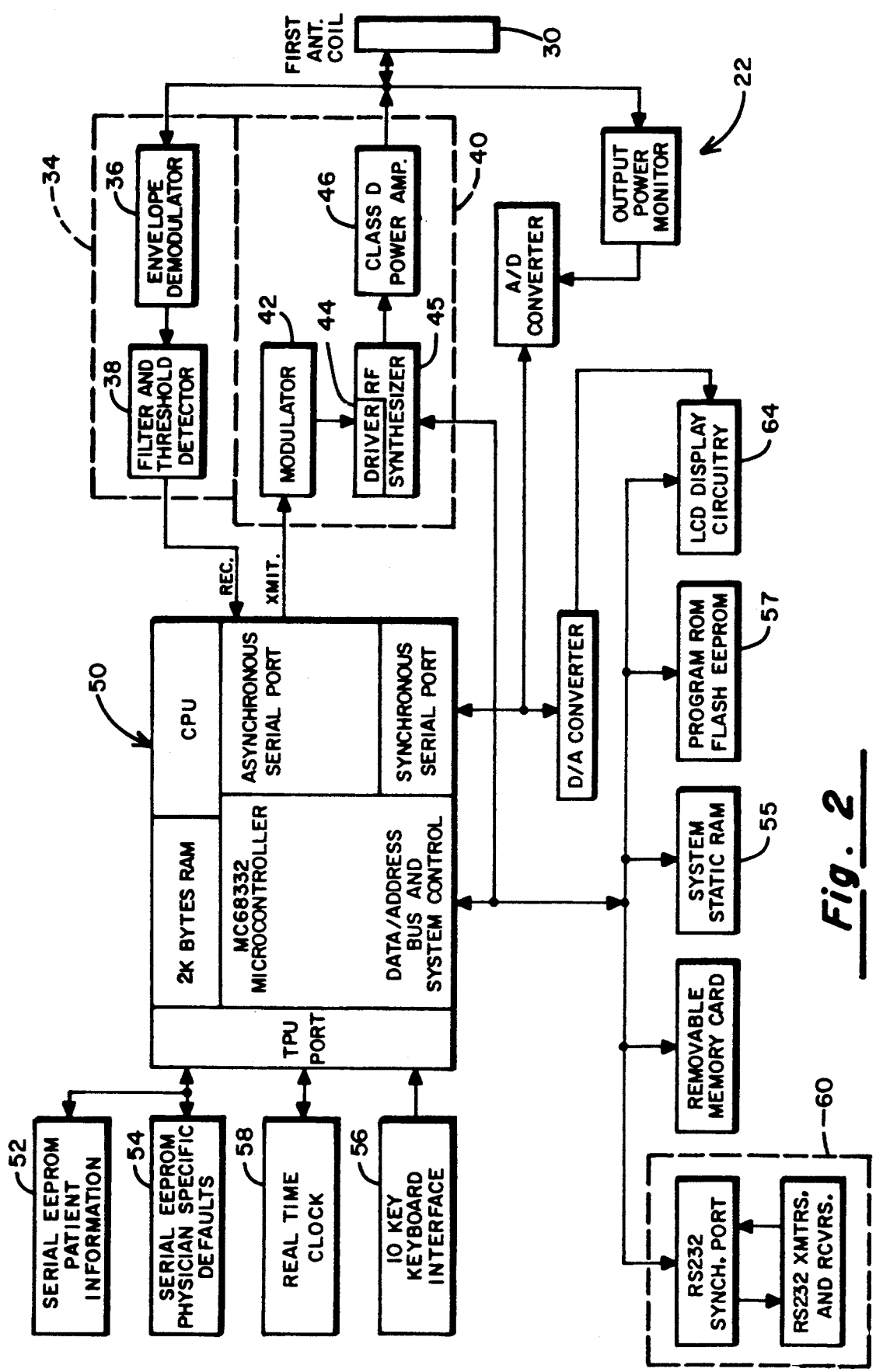
FIG. 2 is a block diagram of the external controller portion.

A preferred embodiment of the invention is illustrated in FIGS. 1-16.

FIG. 1 shows a simplified block diagram of the regenerative electrical stimulator device 20. The external controller portion 22 has a first antenna coil 30 located exterior the body. The stimulator portion 24 with a second antenna coil 32 is intended to be surgically implanted in the patient close to skin barrier 25. The stimulator portion 24 connects by way of the cable 26.1 to electrodes 26 which are placed in proximity to damaged nerve tissue. The rechargeable battery 28 provides the operating power for the stimulator portion 24 and provides the power for the electrical stimuli presented to the electrodes 26.

The first antenna coil 30 emits electromagnetic radiation, represented as arrow 23, and is utilized for the in-link and out-link telemetry for the external controller portion 22 and provides the power for recharging the rechargeable batteries 28. "In-link" telemetry being defined as the transmission of signals by the external controller portion 22 into the implanted stimulation portion 24. "Out-link" telemetry being the transmission of data out from the stimulator portion 24 to the external controller portion 22. The electromagnetic radiation is comprised of a modulated carrier wave operating in the range of 2 megahertz (MHz) that crosses the skin barrier 25 where it is received by the second antenna coil 32.

The second antenna coil 32 is utilized for in-link and out-link telemetry for the stimulator portion 24 and also receives the power for recharging the batteries 28. The out-link telemetry is accomplished by modulating electromagnetic radiation which is reflected back to the first antenna coil. The reflected electromagnetic radiation is indicated by arrow 27.

All of the functions of the external controller portion 22 and the stimulator portion 24 are controlled by their respective control processors.

External Controller Portion

FIG. 2 is a detailed block diagram of the external controller portion. The principal circuits comprising the invention are the receiver circuits 34, the transmitter circuits 40, the first process controller 50, electrically erasable programmable read only memories (EE-PROMS) 52, 54, a keyboard interface 56, a real time clock 58, the LCD display circuitry 64, and a personal computer interface 60. The first antenna coil 32 connects to the transmitter portion 40 which includes a modulator 42, a radio frequency (RF) synthesizer 44, a driver 45, and a class D power amplifier 46.

Figure 3:
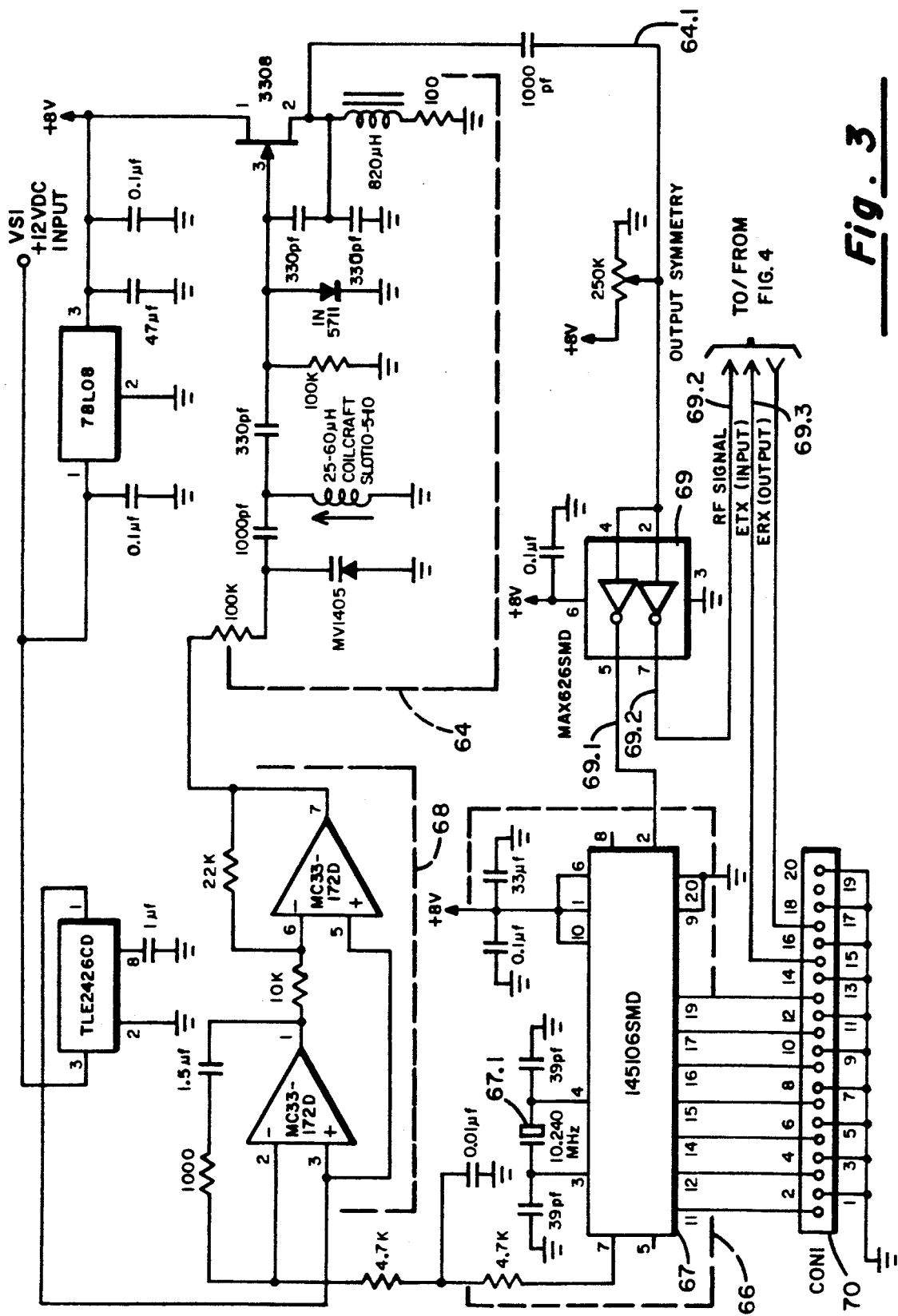
FIG. 3 is a schematic diagram of the radio frequency synthesizer of the external controller portion.

FIG. 3 shows a schematic diagram of the RF synthesizer of the transmitter portion 40 of the external controller portion 22. The RF synthesizer 44 has several subcircuits comprised of the voltage controlled oscillator (VCO) 64, the phase locked loop 66, and the low pass filter 68. The phase locked loop integrated circuit 67 utilized in the preferred embodiment is a Motorola MC 145106. The integrated circuit 67 utilizes an external crystal with a frequency of 10.240 MHz. The integrated circuit 67 divides the 10.240 MHz frequency into an internal reference frequency which is compared to the frequency of the voltage controlled oscillator 64. The output of this comparison is the loop error voltage which goes from the integrated circuit 67 to the low pass filter 68 where the reference signal frequency component is removed. The error voltage is then applied to the voltage controlled oscillator 64 to adjust the frequency of the voltage controlled oscillator 64. In the preferred embodiment, the frequency of the RF synthesizer 44 is set at two MHz, however it is programmable by sending a frequency programming command from the control processor 50 to the phase locked loop integrated circuit 67. The programming connections of the integrated circuit 67 connect to the terminals on the CON1 connector 70. The corresponding terminals of CON1 connector 70 are on FIG. 11.

The output of the voltage controlled oscillator 64 goes via conductor 64.1 to the CMOS buffer amp 69, a Maxim MAX626SMD integrated circuit, which has dual outputs, one output looping back to the integrated circuit 67 by way of conductor 69.1 and the other output providing a symmetrical RF signal through conductor 69.2 for the driver amplifier 72 and the power amplifier 46.

Figure 4:
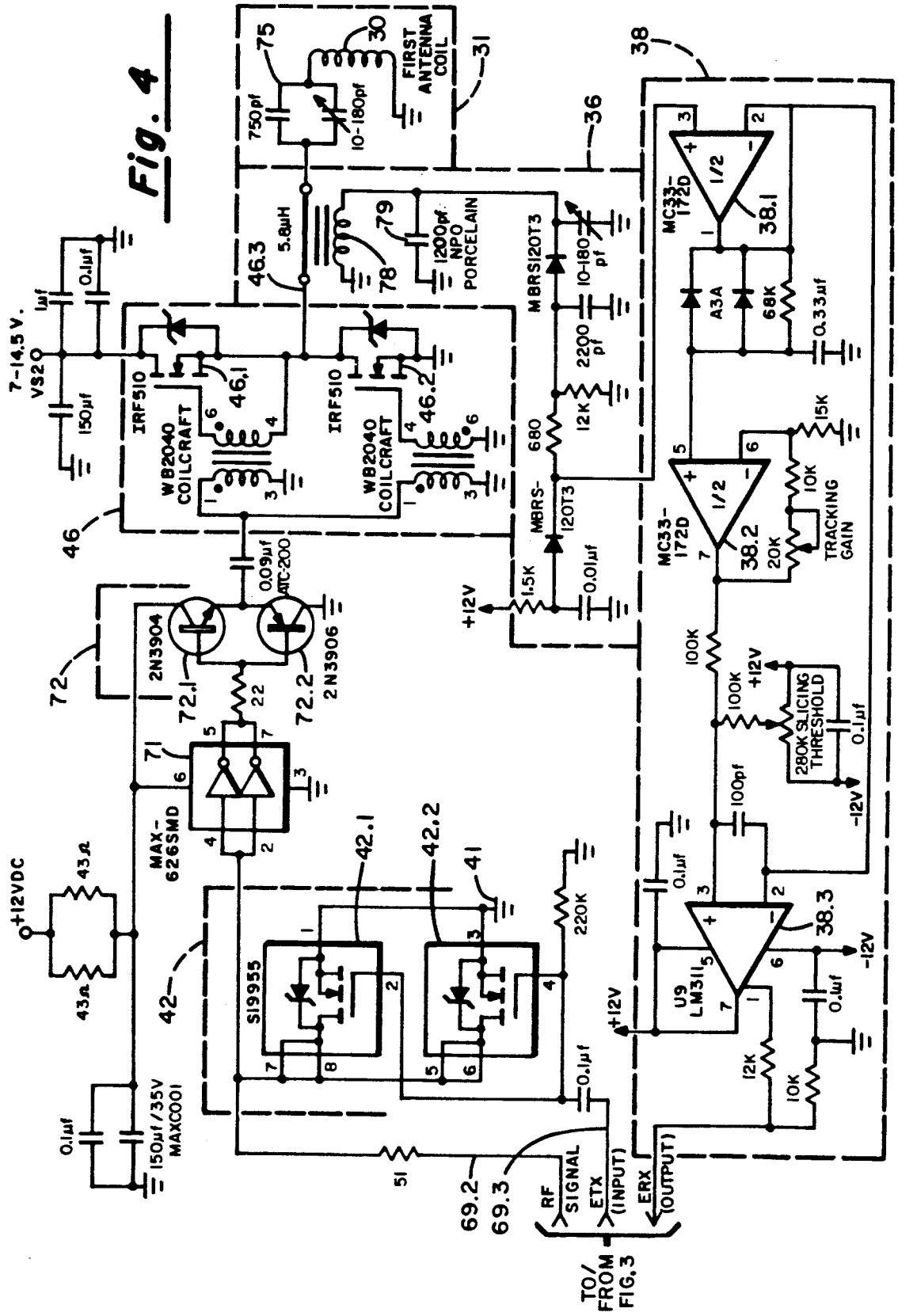
FIG. 4 is a schematic diagram of the modulator, the driver, the class D power amplifier, and the receiver portion of the external control portion.

Referring to FIG. 4, the driver 72 and class D power amplifier 46 are shown. The driver amplifier 72 consists of a pair of bipolar transistors 72.1 and 72.2 and receives the RF signal from conductor 69.2 after it has passed through the buffer amplifier 71. The power amplifier is comprised of a pair of IRF510 power MOSFETS 46.1, 46.2 configured as a class D power amplifier 46. The output of the class D power amplifier 46 is connected through conductor 46.3 to a series resonant tank circuit comprised of the capacitors 75 and the first antenna coil 30. The first antenna coil 30 radiates the RF energy and couples with the second antenna coil 32 of the stimulator portion 24 when they are in proximity to each other. The tank circuit thus constitutes a tuned primary circuit 31. The two MHz radio frequency (RF) signal provides the power transfer for recharging the batteries of the implanted stimulator portion 24.

The in-link telemetry modulation is provided by the modulator 42 which acts to switch the output of the voltage controlled oscillator 64 to ground, thus grounding the RF signal and eliminating the RF input to the drive amplifier 72 and the power amplifier 46. The modulator 42 in the embodiment shown consists of two Siliconix Si9955 metal-oxide-semiconductor field-effect transistors (MOSFETS) 42.1, 42.2 connected between the ground and the conductor 69.2, shown in FIG. 3. The operating signal for the modulator 42, designated "ETX" on FIGS. 3 and 4, is received by way of conductor 69.3, and is the serial data output from the control processor 50 containing the commands to be sent to the stimulator portion 24. The serial data operates to amplitude shift key the radio frequency output of the power amplifier 46. Conductor 69.3 connects to the CON1 connector 70 with the corresponding connecting terminal shown on FIG. 11. The serial data output constituting the in-link telemetry signal is designated "TX" on FIGS. 6b, 10 and 11.

The receiver or out-link telemetry circuitry for the external controller portion 22 is also shown on FIG. 4. The secondary of the transformer 78, and capacitor 79, form a tuned circuit. The transformer 78 has a single turn primary which picks up the current in conductor 46.3 and induces a voltage in the secondary of transformer 78. The voltage induced in the secondary of 78 fluctuates in accordance to the out-link telemetry signal from the stimulator portion 24 which is comprised of reflected RF energy. The method of reflecting and modulating the RF energy in the stimulator portion 24 is discussed below with reference to FIG. 13a.

Continuing to refer to FIG. 4, the envelope demodulator circuitry 36 detects the encoded signal, filters the rf, and provides the signal to the tracking and threshold detector 38. The tracking and threshold detector 38 compensates for variations in positional alignments between the first antenna coil 30 and the second antenna coil 32 and also compensates for motion between the coils 30, 32 during operation. The tracking and threshold detector 38 utilize three operational amplifiers 38.1, 38.2, 38.3 configured as an automatic gain control with a threshold crossing detector. The three operational amplifiers are available from Motorola Inc. and are identified as MC33172D, MC33172D, and LM311 respectively. The third operational amplifier 38.3 operates as a comparator, comparing an averaged value of the pulsed wave form to the actual serial pulse wave form, the output providing stable, uniform serial data pulses. The serial data pulses are then forwarded to the microcontroller 50 for processing.

Figure 5:
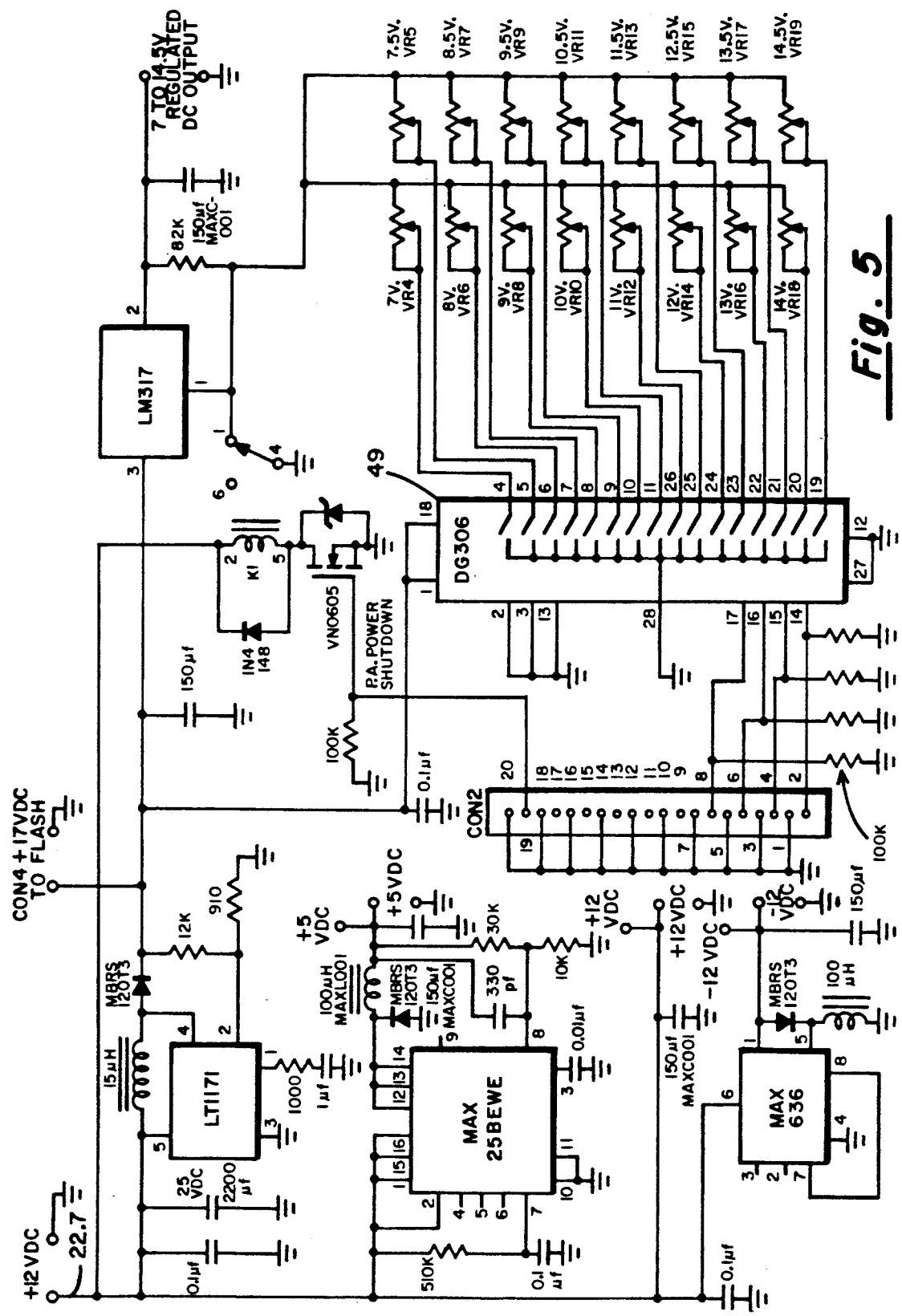
FIG. 5 is a schematic diagram of the power supply circuity for the external controller portion.
Figure 6A:
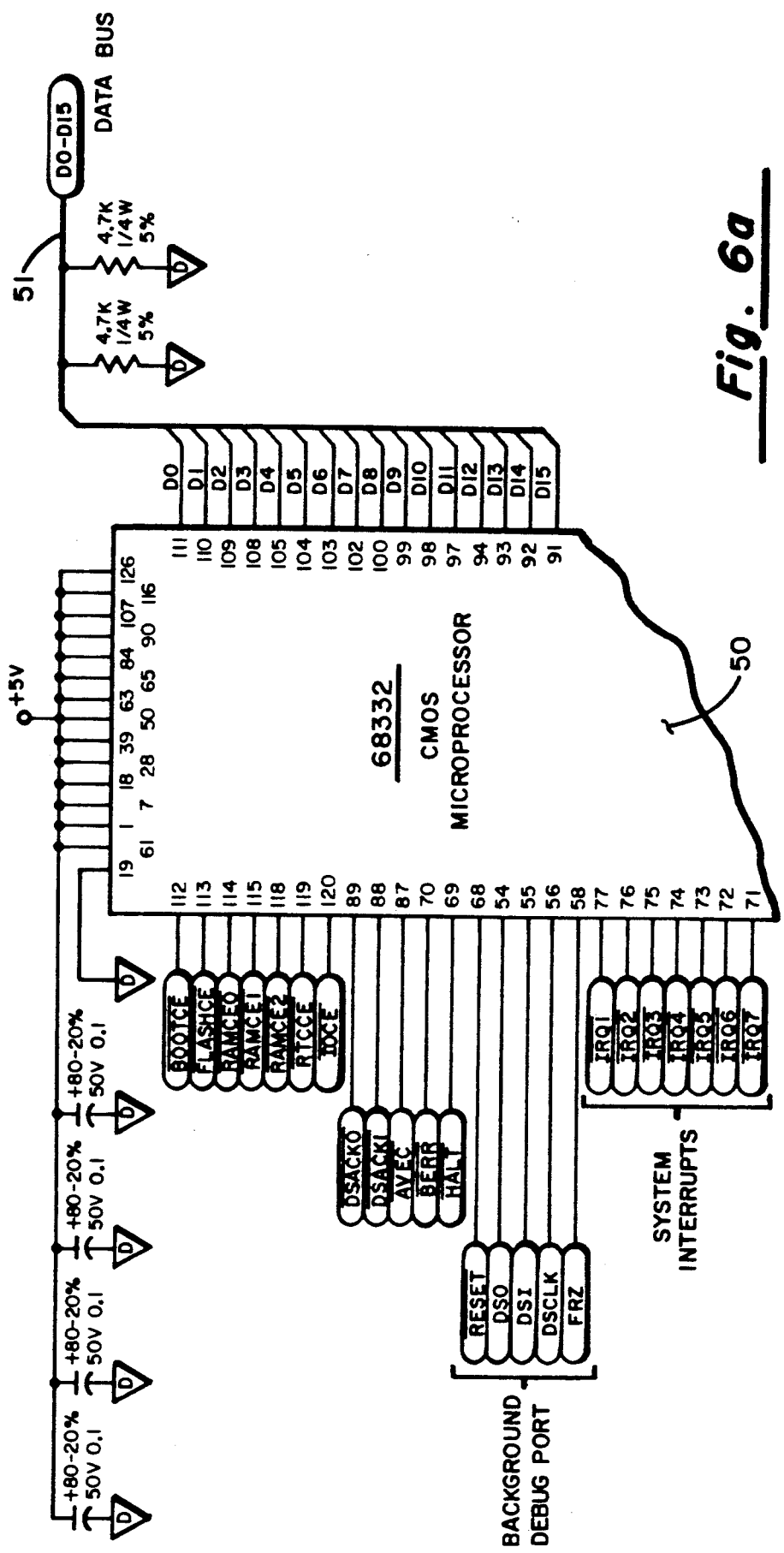
FIGS. 6a and 6b are schematic diagrams of the control processor integrated circuitry for the external controller portion.
Figure 6B:
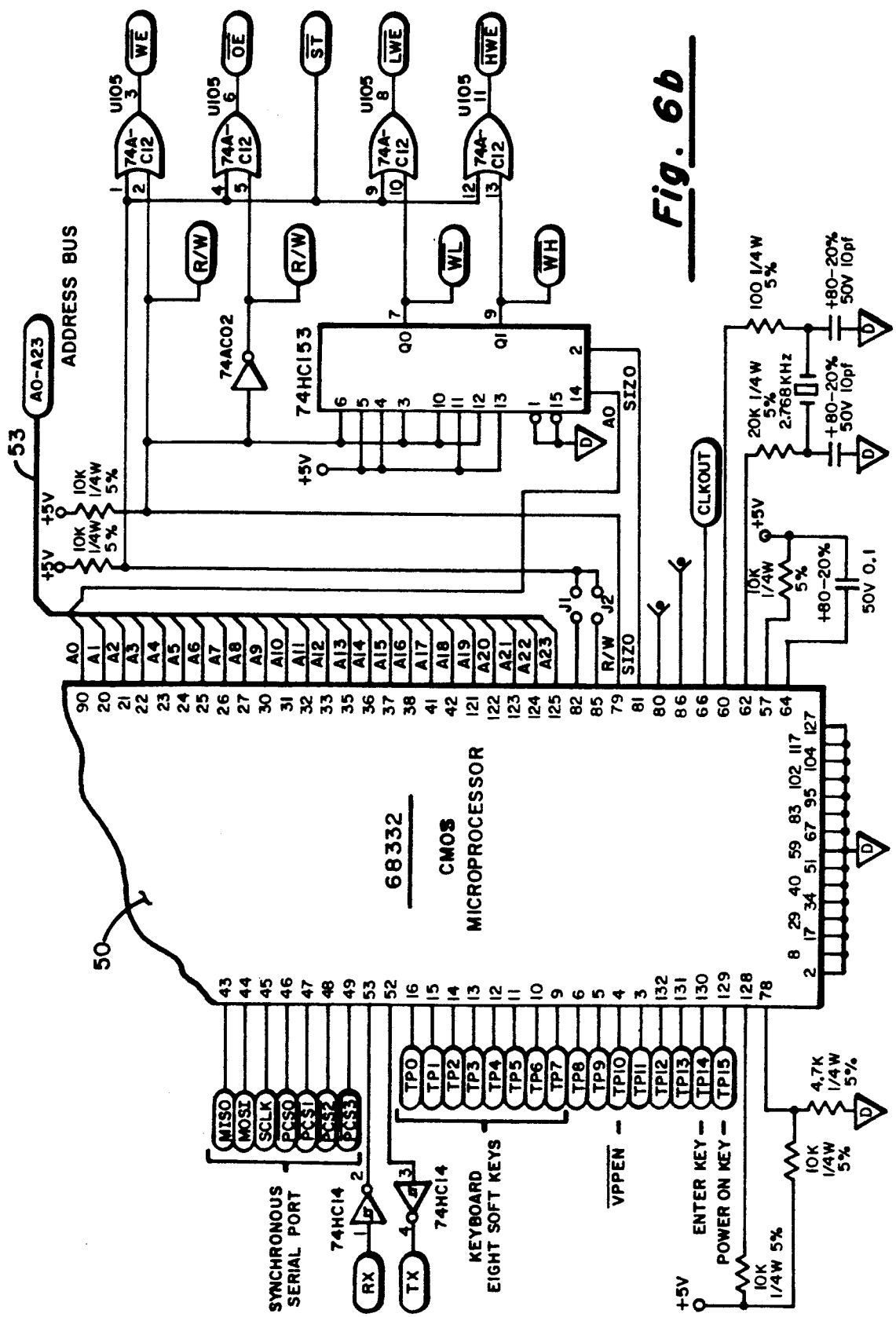

FIG. 5 shows a schematic of a programmable power supply for the external controller portion 22. The power supply supplies the necessary power for all of the circuits of the external controller portion 22. Notably, the output of the power supply is programmable to provide incrementally adjustable voltage to the class D power amplifier 46 by way of commands from the control processor 50 to integrated circuit 49 thereby adjusting the RF output level. Integrated circuit 49 is a CMOS analog switch available through Maxim Integrated Products, 120 San Gabriel Drive, Sunnyvale, Calif. 94086. The power supply requires 12 volt input at terminal 22.7. The control lines for the integrated circuit 49 connect to the CON2 connector 49. The CON2 connector 49 with the connecting terminals is on FIG. 11.

FIGS. 6a, 6b, 7, 8, 9, 10, and 11 show schematic drawings of the control processor circuitry and the related operating and memory circuitry for the external controller portion 22. The various signal lines on the figures showing the digital circuitry, FIGS. 6a, 6b, 7, 8, 9, 10, 11, 14, 15, and 16, are labeled with conventional terminology. The labels enclosed in ovals indicate that that specific line connects to all other like-labeled lines. The control processor 50 utilized in the preferred embodiment is a Motorola, Inc. MC 68332 integrated circuit. The MC 68332 is a 32 bit micro-controller with 2K bytes of fast static RAM, an asynchronous serial interface, a synchronous serial interface, a time processor unit, seven interrupt lines, chip select outputs, and bus control circuitry.

For specific information on the specifications, the technical information, and the details of programming and operation of the MC 68332, see *User's Manual*, document No. MC 683324M/AD, by Motorola, Inc., distributed by Motorola Literature Distribution, P. 0. Box 20912, Phoenix, Ariz.; and also see the MC 68332 Motorola Semiconductor Technical Data, document No. MC 68332TS/D, 1990, also distributed by Motorola Literature Distribution.

Figure 7:
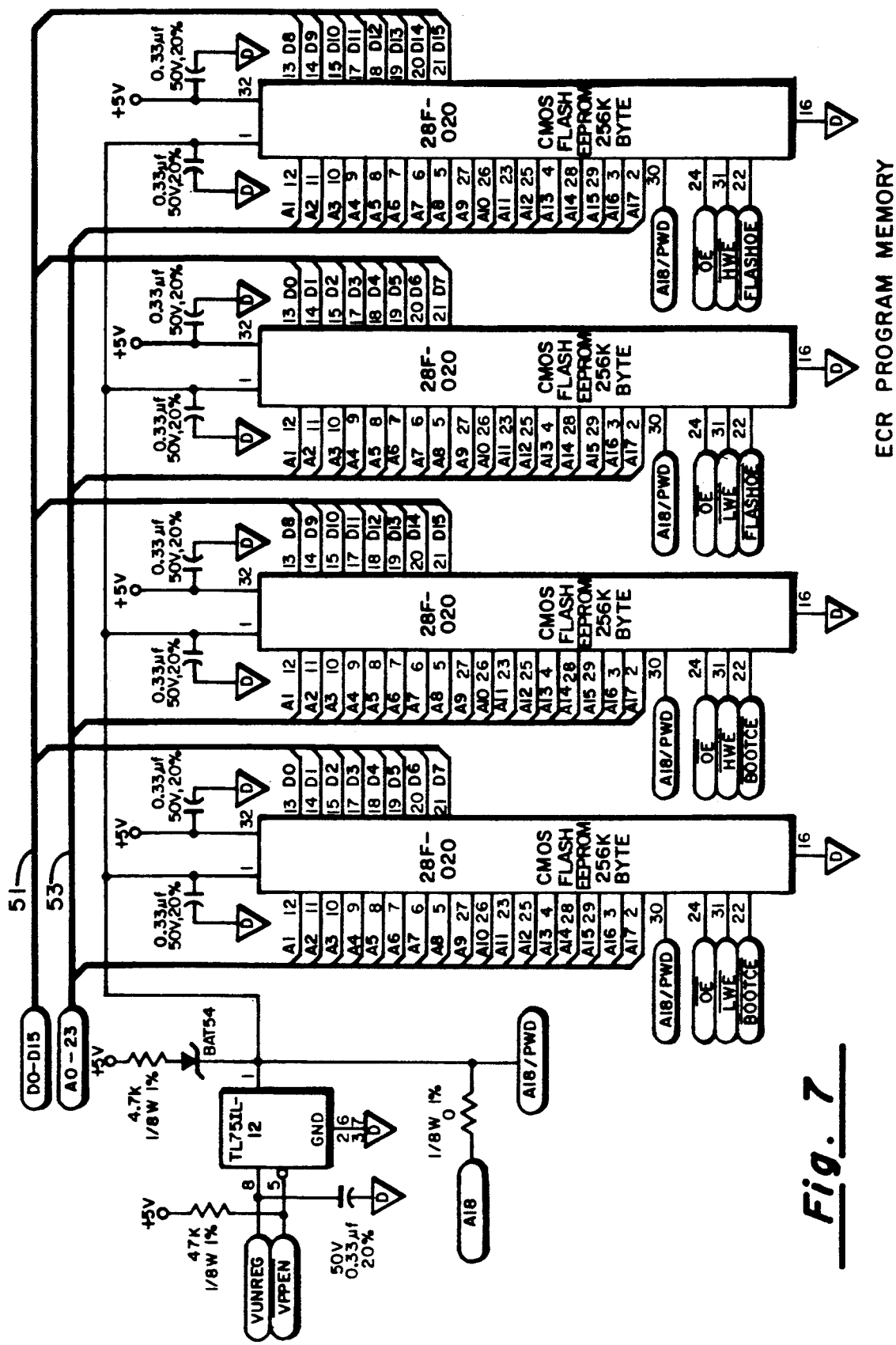
FIG. 7 is a schematic diagram of the integrated circuits comprising the program memory circuitry of the external controller portion.
Figure 8:
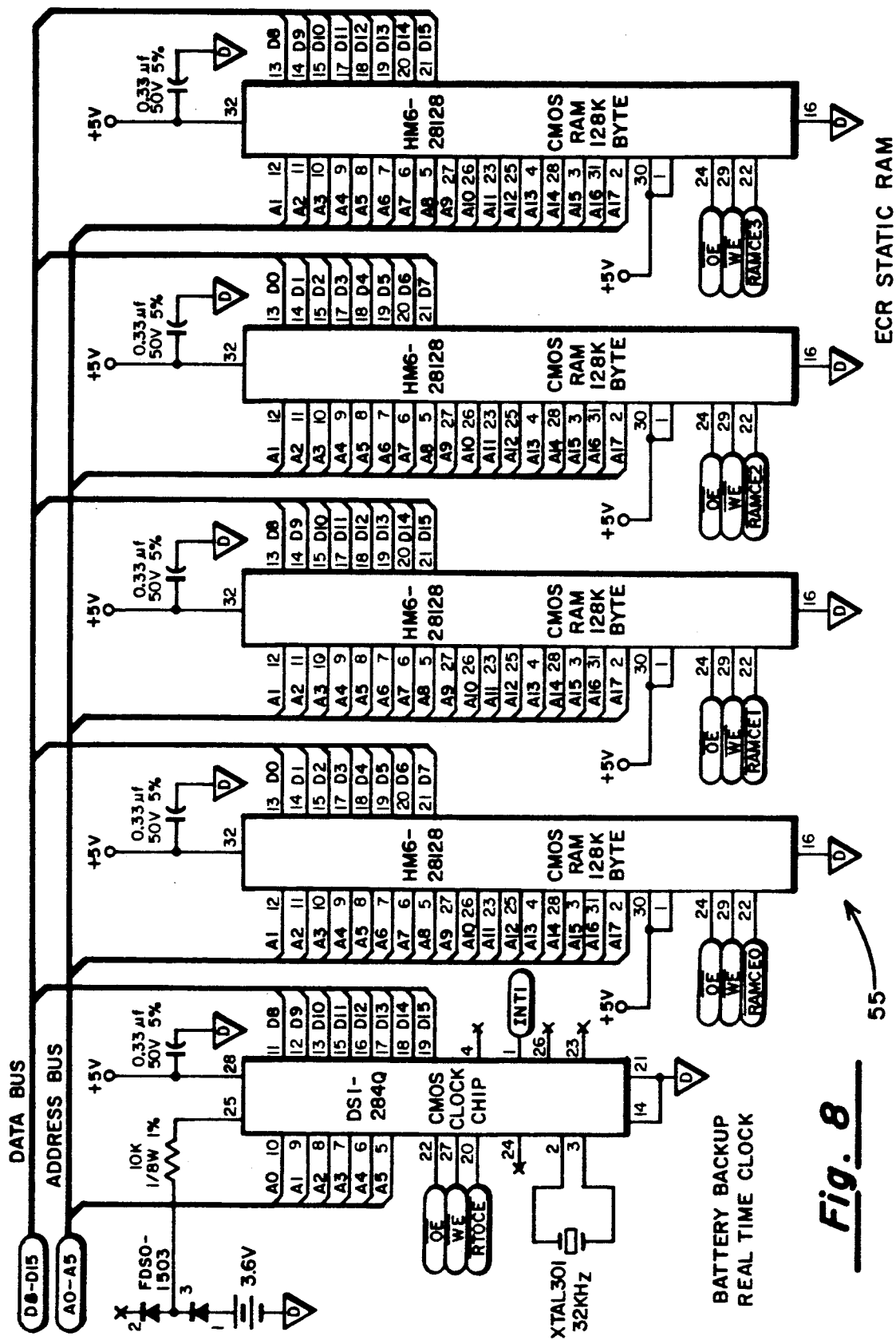
FIG. 8 is a schematic diagram of the static random access memory and the real time clock circuitry of the external controller portion.

As shown in FIG. 8, the address bus 53 and data bus 51 connect the first control processor 50 to the system static RAM 55 comprised of four HM628128 integrated circuits. FIG. 8 also shows the real time clock 58 with battery back up allowing data recorded to be time stamped. As shown in FIG. 7, the address bus 53 and data bus 51 also connect the first control processor 50 to the program ROM circuitry 57 comprised of four 28F020 FLASH EEPROM (electrically erasable programmable read only memory) integrated circuits. The FLASH memory allows the programming to be stored indefinitely. The Programs may be modified by way of a personal computer serially connected to the first control processor 50 by way of the personal computer interface 60 shown in FIG. 11.

Figure 9:
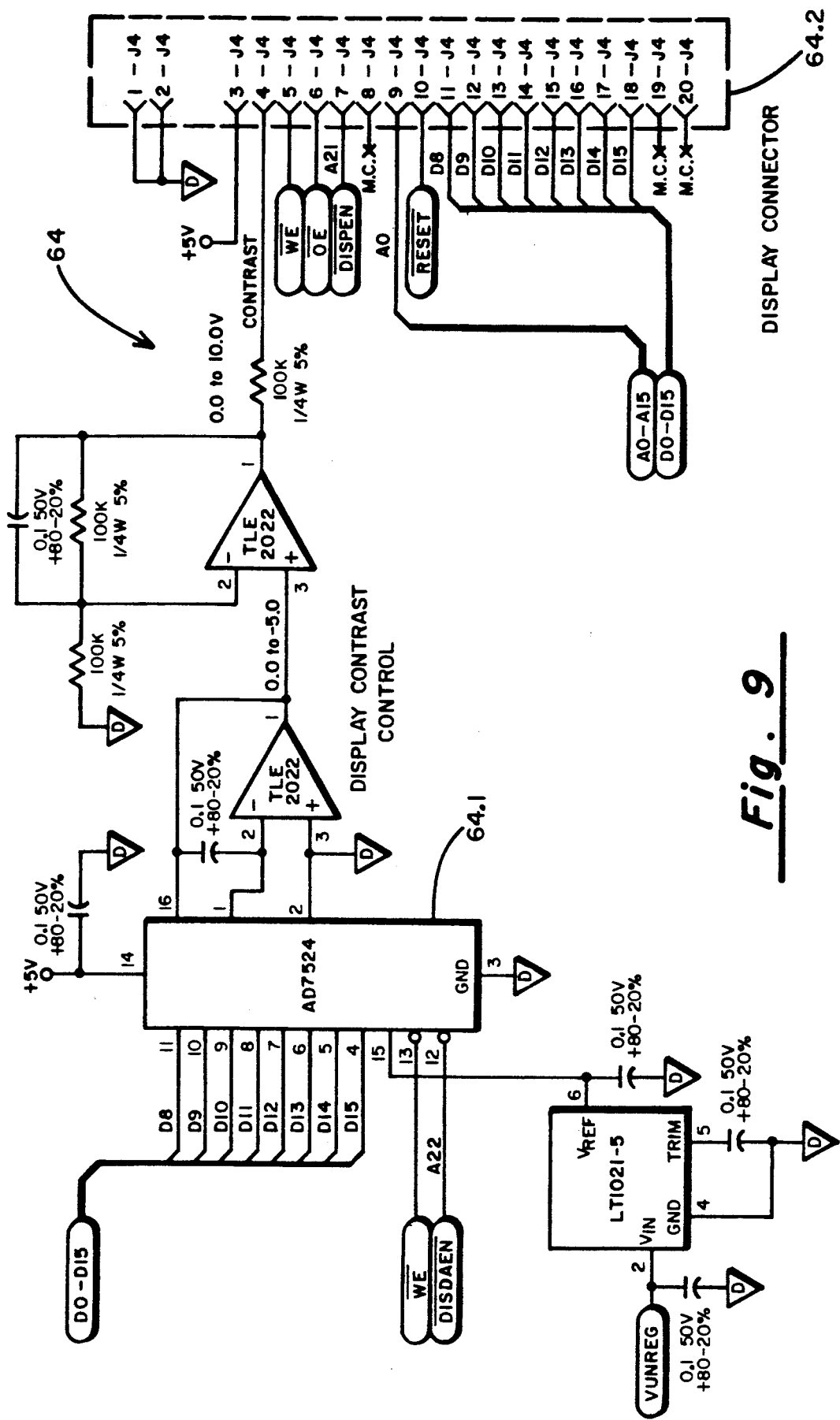
FIG. 9 is a schematic of the circuitry for the display interface of the external controller portion.

FIG. 9 shows the LCD display circuitry 64. The LCD is not shown but is of conventional design and is connected by way of the J4 connector 64.2. Contrast is controlled by way of a digital/analog converter 64.1 manufactured by Analog Services, Inc., One Technology Way, Norwood, Mass. 02062.

Figure 10A:
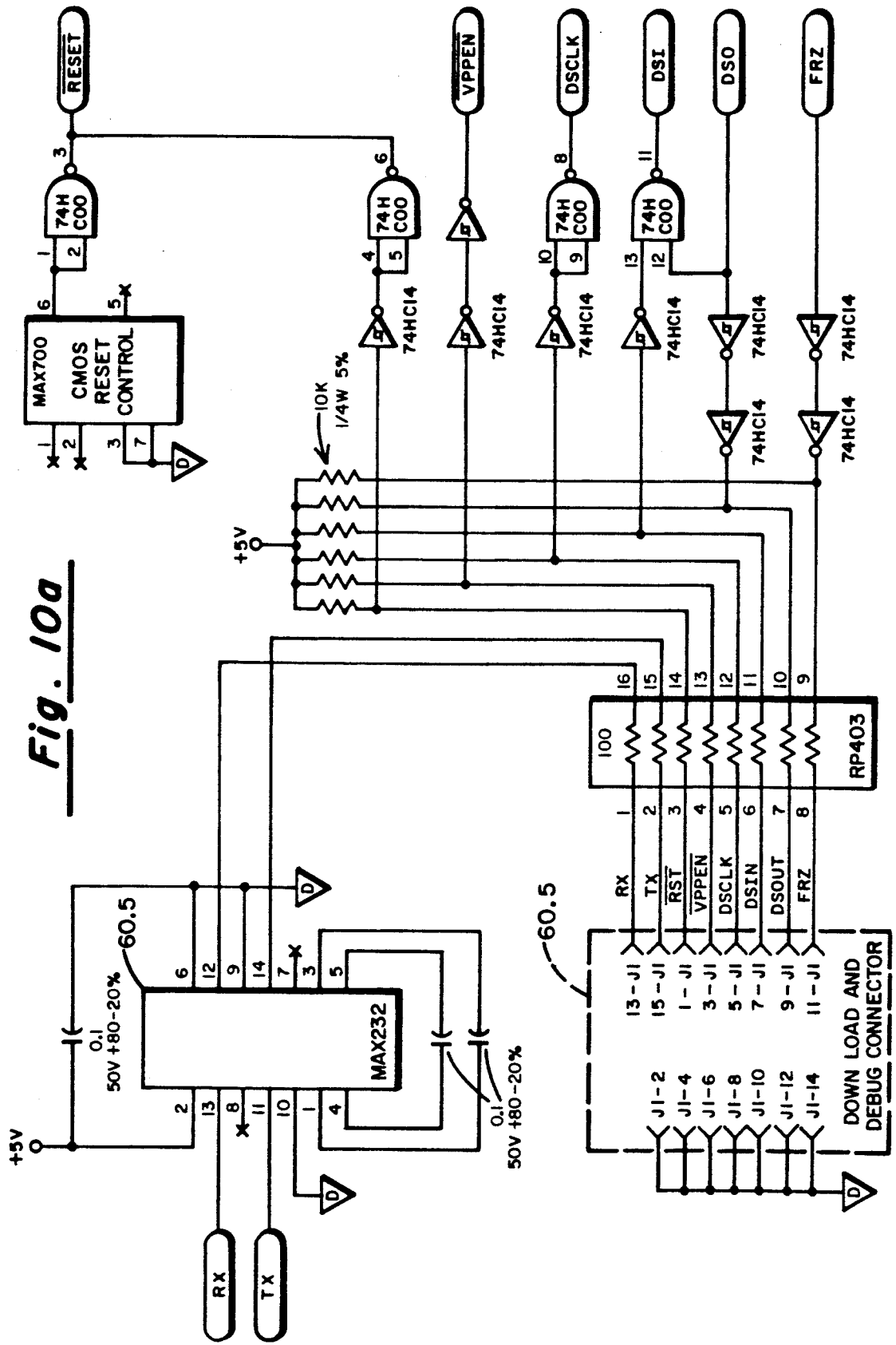
FIGS. 10a and 10b are schematic diagrams of the debugging port circuitry and keyboard connecting circuitry of the external controller portion.
Figure 10B:
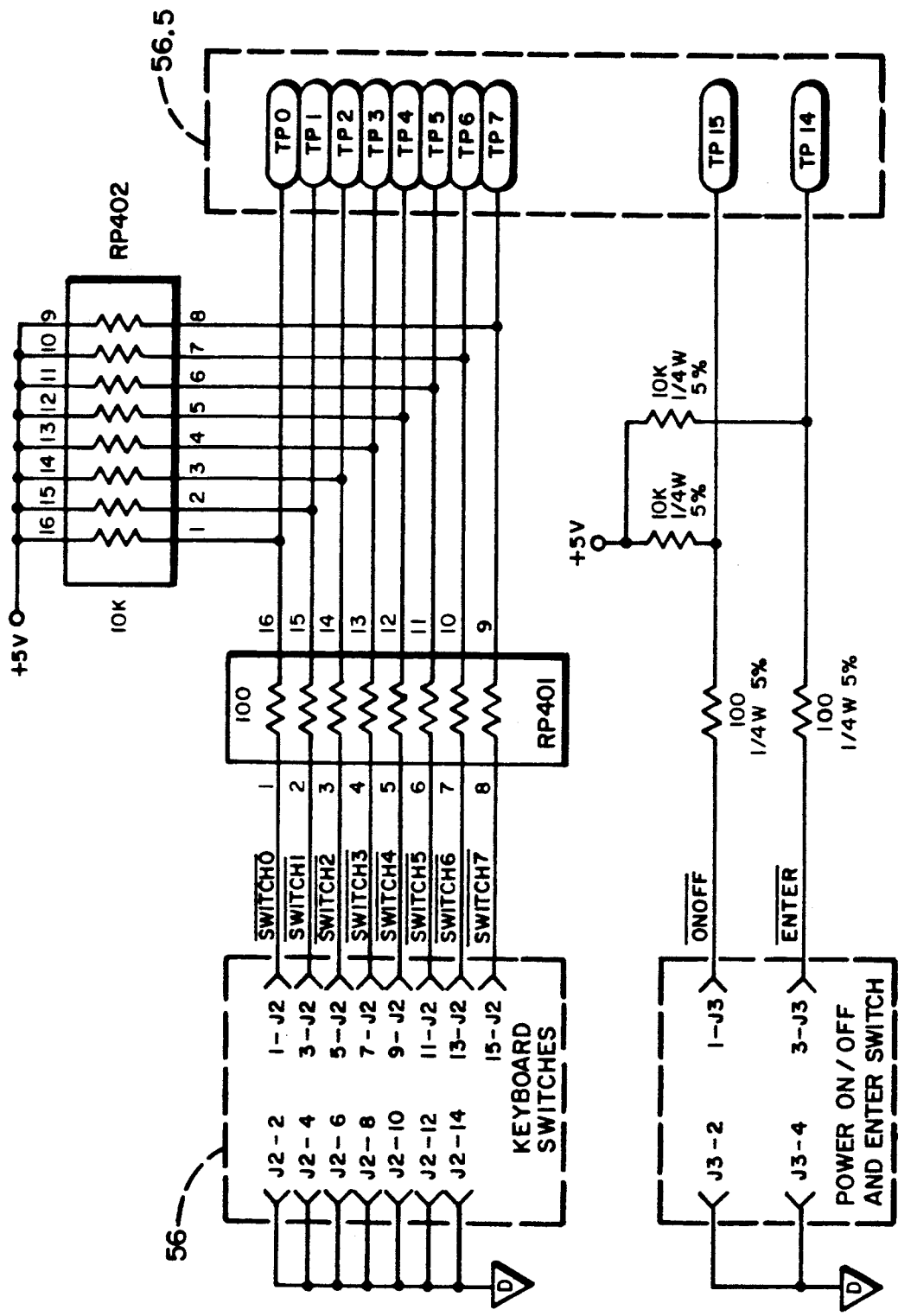

FIG. 10a shows the circuitry for the downloading and debugging port for connection with an external personal computer through the J1 connector 60.5. The serial data signals containing the in-link and out-link telemetry data designated "TX" and "RX" go through the 232 converter 60.5, manufactured by Maxim Integrated Products, Inc., for compatibility with the personal computer. Similarly, the other signal lines to and from the first control processor 50 are appropriately conditioned. FIG. 10b shows the circuit location for the keyboard switches (not shown) for operating the external control portion 24 at the J2 connector 56. The signal lines 56.5 connect to the first control processor 50 shown on FIG. 6b. FIG. 10b also shows the J3 connector 60.3 for connecting a power On/Off switch (not shown) and an "enter" switch (not shown).

Figure 11A:
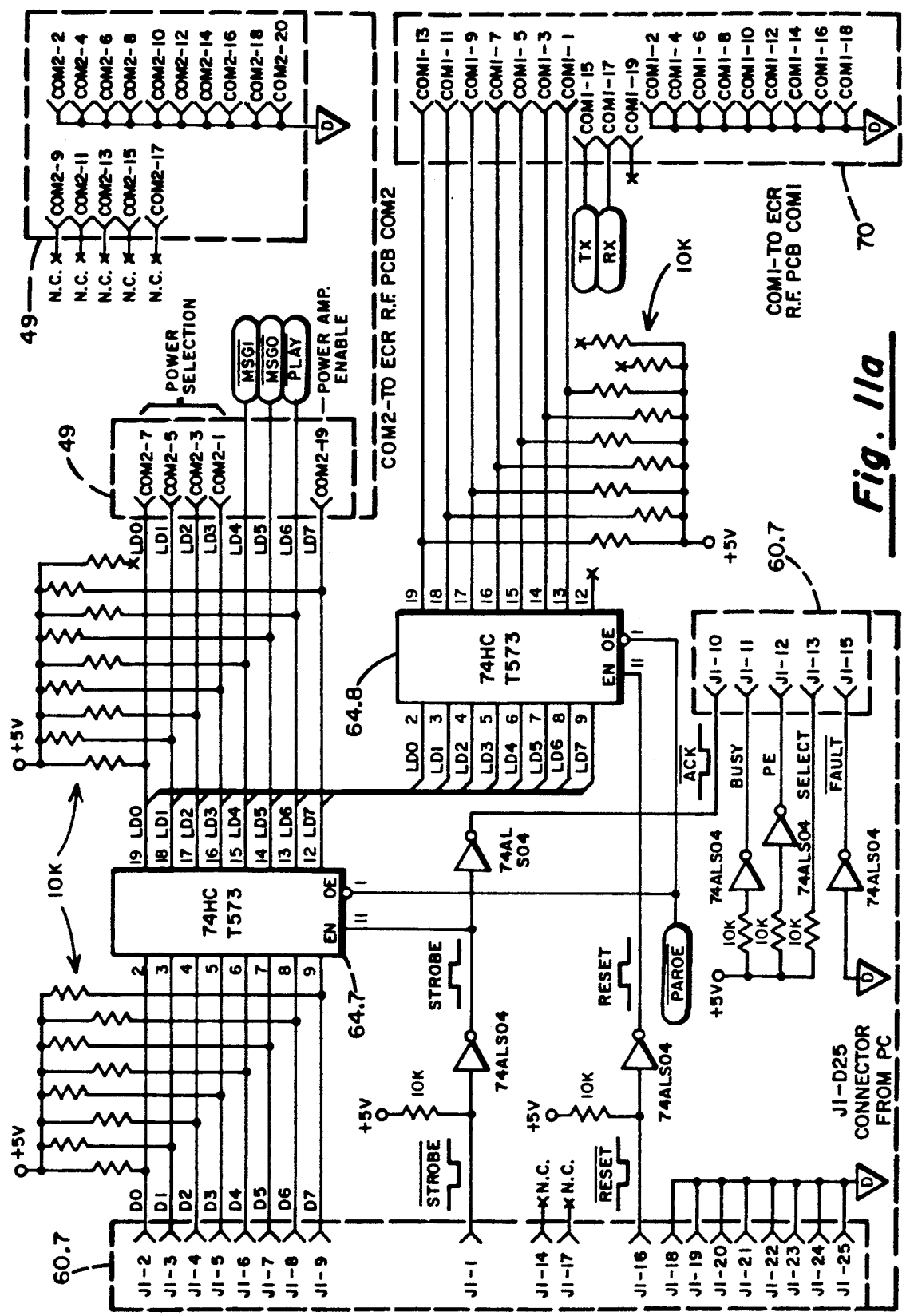
FIGS. 11a and 11b are schematic diagrams of the personal computer interface circuitry of the external controller portion.
Figure 11B:
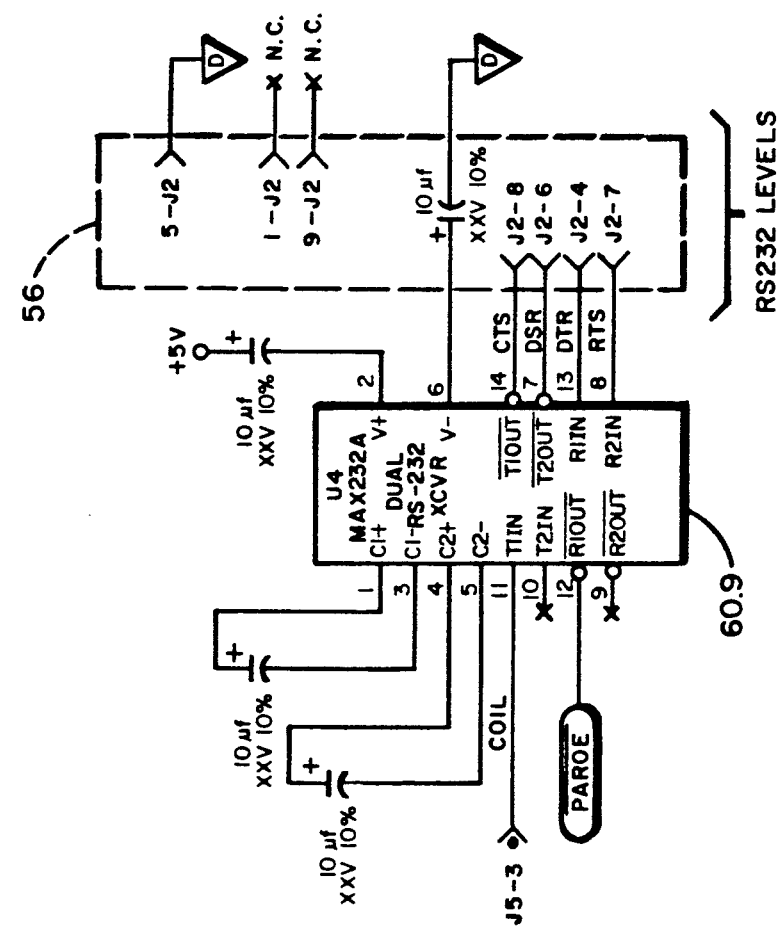

FIG. 11a shows the circuitry for interfacing the device with a personal computer. The 25 pin J1 connector 60.7 provides the direct linkage with the personal computer. Also shown are the CON1 connector 70 and the CON2 connector 49 which connect the RF telemetry and power supply circuits to the digital circuits and two latches 64.7, 64.8. FIG. 11b shows an additional 232 converter 60.9 and terminals for the J2 connector 56 also shown in FIG. 10a. The 232 converter 60.9 is also manufactured by Maxim Integrated Products, Inc.

Antenna Coils

As previously indicated, the first antenna coil 30 couples with the second antenna 32 coil to transcutaneously provide power for recharging the batteries of the stimulator portion 24 and to provide in-link and out-link telemetry. The antenna coils are configured in series tuned circuits which provide a low impedance primary tuned circuit 31 which is desirable for operation with the class D power amplifier 46 and a low impedance secondary tuned circuit 33 which is compatible to the secondary tuned circuit load.

The design and specification of the first and second antenna coils 30, 32 was dependant on the load presented to the second antenna coil, the circuit configurations, the coupling coefficient, the inductances and the desired physical dimensions. An appropriate size for the second antenna coil 32 for the implantable stimulator portion 24 was determined to be one inch. Extensive analysis and experimentation yielded the values for the preferred embodiment which are presented in Table 1 below.

TABLE 1

|  | First Antenna Coil 30 | Second Antenna Coil 32 |
| --- | --- | --- |
| Coil diameter | 1.25 in. | 1.00 in. |
| Axial thickness | 0.125 in. | 0.125 in. |
| Radial thickness | 0.025 in. | 0.025 in. |
| No. of turns | 10 turns | 13 turns |
| Wire | Litz Wire | AWG No. 30 copper |
| Inductance | 5.8 μH | 8.0 μH |

The Litz wire for the first antenna coil is comprised of single nylon polyester covered copper wire, 175 strands of AWG 48, available from Kerrigan-Lewis, Inc. The above design provides adequate tolerance room for variation in coil separation and misalignment. The design separation between the coils is ¼ inch, however, the device will operate satisfactorily with significant variation from this dimension.

The first antenna coil in the preferred embodiment is encapsulated in silicon rubber and is connected by way of cable to the external controller portion 22. Attachment to the skin of the patient for recharging and/or telemetry may be accomplished by way of adhesive tape or other products such as Tegaderm TM available from Minnesota Mining and Manufacturing Company, St. Paul, Minn. The second antenna coil is included in the stimulator encapsulated portion 24.

Implantable Stimulator Portion

FIG. 12 shows a detailed block diagram for the implantable stimulator portion 4. The second antenna coil 32 is connected to the battery charging circuits 80 for providing the power to recharge the batteries 28; the antenna coil 32 is connected to the envelope demodulator 82 and threshold detector 84 to provide the in-link telemetry; and the antenna coil 32 is also connected to the passive telemetry transmitter 86 to provide the out-link telemetry.

The envelope demodulator 82 and threshold detector 84 input to the serial interface portion of the second control processor 90 for processing the in-link telemetry. Similarly, the serial interface of the second control processor provides the out-link telemetry data to the passive telemetry transmitter 86. The second control processor 90 further receives data from the charging sense circuits 92, electrode current and voltage data from the electrode current and voltage sense circuits 94. The data is input into the analog-to-digital converter portion of the second control processor 90. The second control processor 90 controls the output of the electrodes 26 by way of the digital/analog circuits 98, the current mirror 97, and the analog switches 95.

Figure 13A:
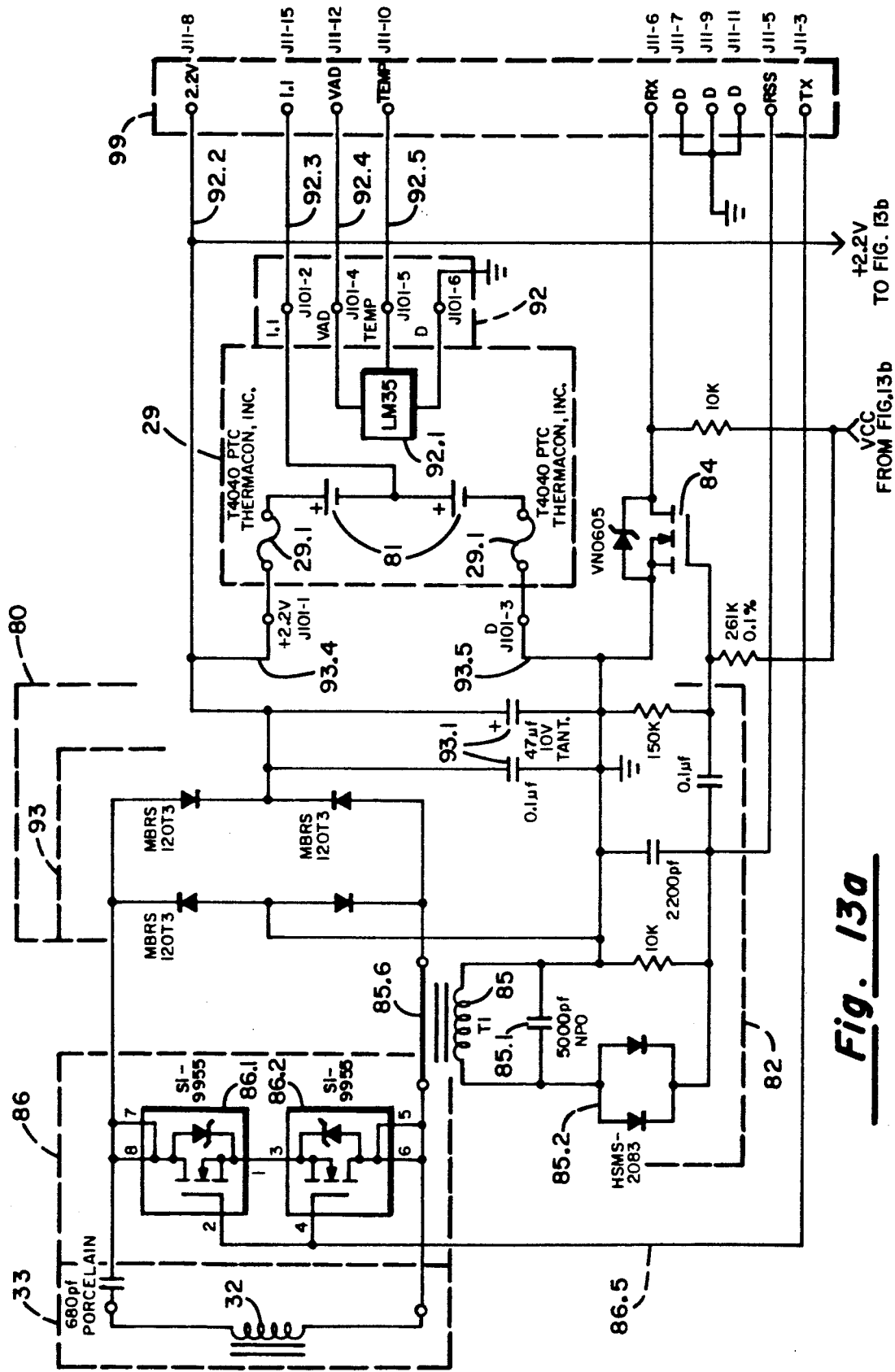
FIG. 13a is a schematic diagram of the passive transmitter, envelope demodulator and threshold detector for the stimulator portion.

FIG. 13a shows a schematic diagram of the circuitry for a preferred embodiment for the passive telemetry transmitter 86, the envelope demodulator 82, threshold detector 84, the battery charging circuits 80, and the rechargeable battery pack 29. The second antenna coil 32 is shown in series with capacitor 96 forming the secondary tuned circuit 33. The secondary tuned circuit 33 is connected to a full wave bridge rectifier circuit 93 and filtering capacitors 93.1 which comprise the battery charging circuits 80. The full wave bridge rectifier is connected to the battery pack 29 by way of conductors 93.4 and 93.5. In the preferred embodiment, the batteries 81 are nickel metal hydride (NiMH) rechargeable battery cells, size AA, and with a voltage output of 1.2 volts. This type of battery provides an improved energy density over other types of rechargeable batteries such as nickel cadmium (NiCd) batteries, of the same size. The NiMH batteries are available from Harding Energy Systems, Inc. The battery pack 29 also includes circuit breakers 29.1 to protect against excessive current. The devices in the preferred embodiment are identified as T4040 PTC, manufactured by the Thermacon Company, and are solid state and automatically reset. Also included in the battery pack 29 is a temperature sensor 92.1 for monitoring battery temperatures while recharging. The temperature sensor along with conductors 92.2, 92.3, 92.4, and 92.5 comprise the charging sense circuits. Conductors 92.4 and 92.5 are connected to the temperature sensor 92.1. Conductors 92.2 and 92.3 are connected to the battery cells 81.

The passive telemetry transmitter 86 is comprised of a pair of MOSFET transistors 86.1, 86.2 which are connected across the tuned secondary circuit 33 so that when they are switched "on" the tuned secondary circuit 33 is short circuited. The first antenna coil 30 and second antenna coil 32 couple when they are in proximity to each other. The short circuiting of the tuned secondary circuit 97 operates to reflect electromagnetic radiation back to the tuned primary circuit 31 which is otherwise absorbed by the tuned secondary circuit 32 and connected circuitry. The MOSFETS 86.1, 86.2 are switched in accordance with a signal conveyed on conductor 86.5 from the second control processor 90 to generate the encoded out-link telemetry signal labeled "TX" on FIG. 13a. Conductor 86.5 connects to J11 connector 99 which has corresponding terminals shown on FIG. 15.

The MOSFETS 86.1, 86.2 shown in the preferred embodiment of the passive transmitter are Siliconix Si9955 transistors. In that these MOSFET switches have extremely low power drain and the actual medium which is utilized to transmit the out-link telemetry is RF power reflected from the external controller portion 22, the transmitter is passive and the battery consumption of the out-link telemetry is negligible. The MOSFETS are operated by the second control processor 90 at a rate of 4800 baud.

The envelope demodulator and threshold detector 82 is also shown on FIG. 16a. Transformer 85 has a single wire primary 85.6 and a secondary that is in parallel with capacitor 85.1 forming a tuned circuit. The tuned circuit is connected to a pair of diodes 85.2 and additional RC circuitry whereby the in-link telemetry signal is detected and shaped. The signal then goes to the threshold detector 84 comprised of a MOSFET. The threshold detector 84 presents the received in-link telemetry signal labeled "RX" to the second control processor 90.

Figure 15B:
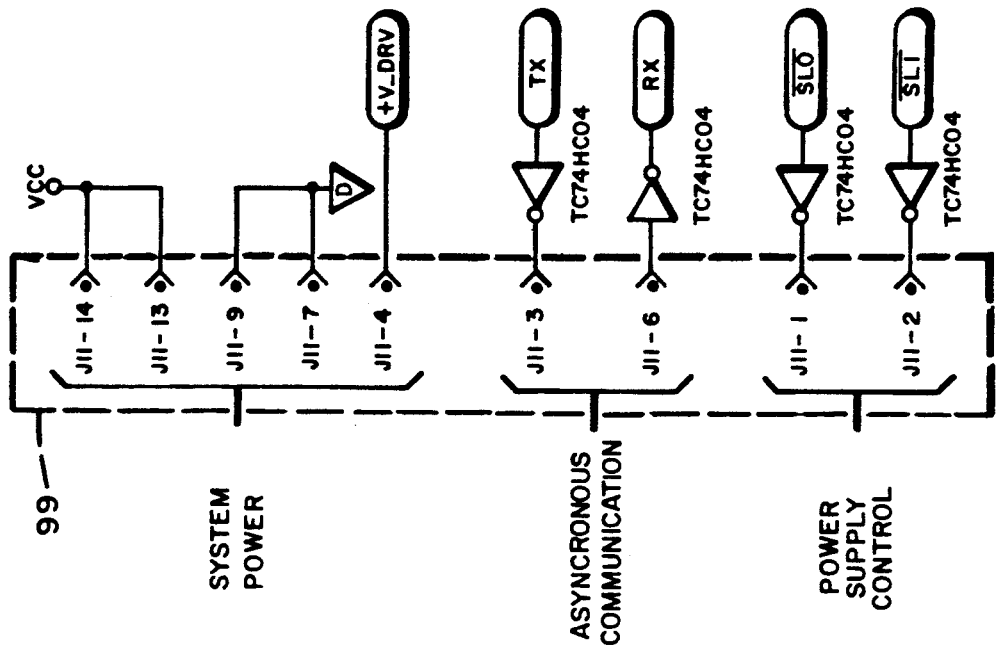
FIGS. 15a and 15b are schematic diagrams of an analog-to-digital convertor, switching circuitry and connector circuitry.

The conductors for the envelope demodulator and threshold detector 82, and the charging sense circuits 92, connect to the connector 99 which has the corresponding terminals shown in FIG. 15.

Figure 13B:
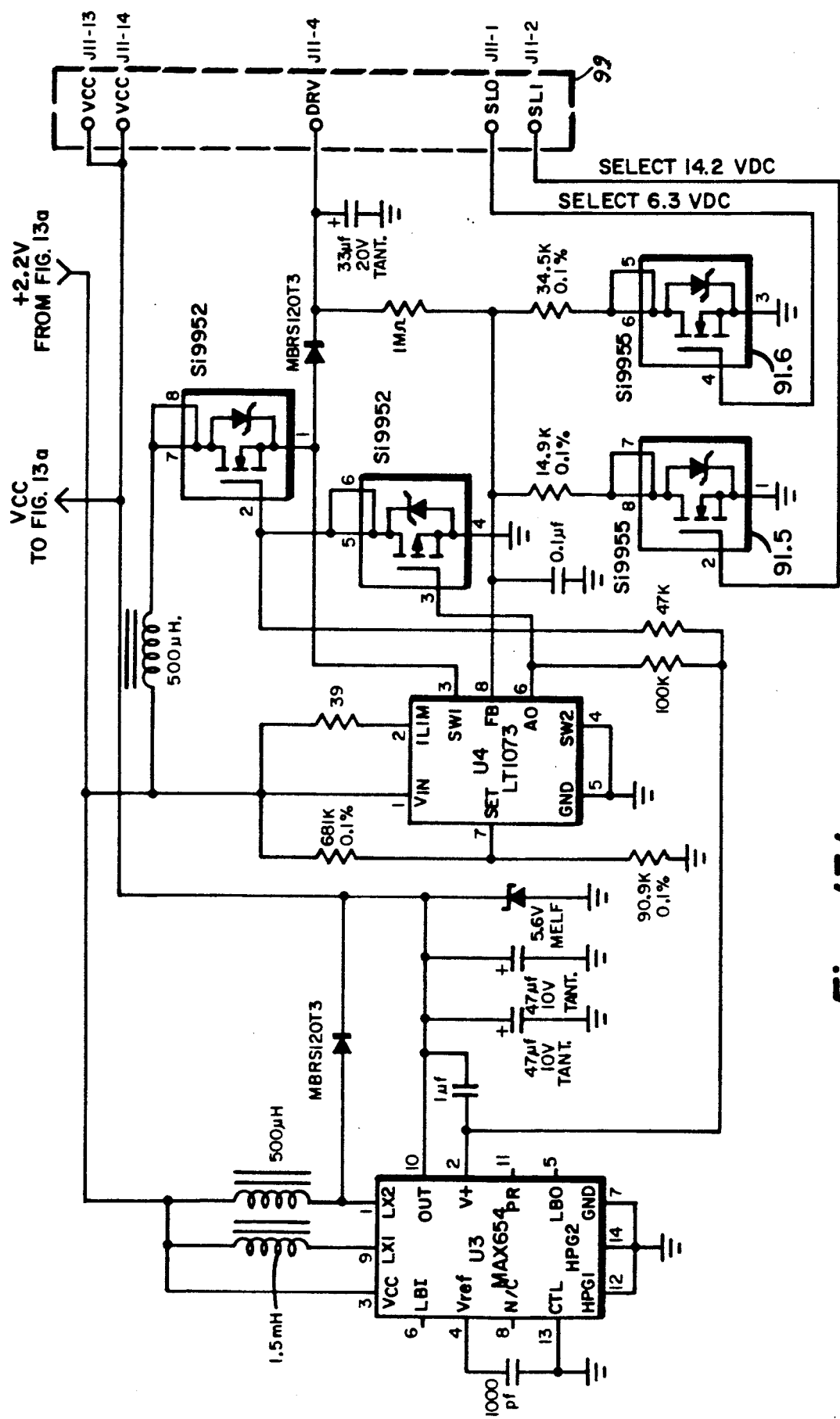
FIG. 13b is a schematic diagram of the power circuitry for the stimulator portion.

FIG. 13b shows the circuitry for system voltage and boost converters 91 for the implantable stimulator portion 24. Battery voltage of 2.2 volts is provided from conductor 91.1. The 2.2 volts is boosted to provide system power and the power for the electrodes 26. Power output for the electrodes 26 is switched by way of the MOSFETS 91.5, 91.6 and is controlled by the second control processor 90. The terminal connections for the system voltage boost converters circuitry 91 is also at the connector 99 with the corresponding terminal connections shown in FIG. 15.

Figure 14A:
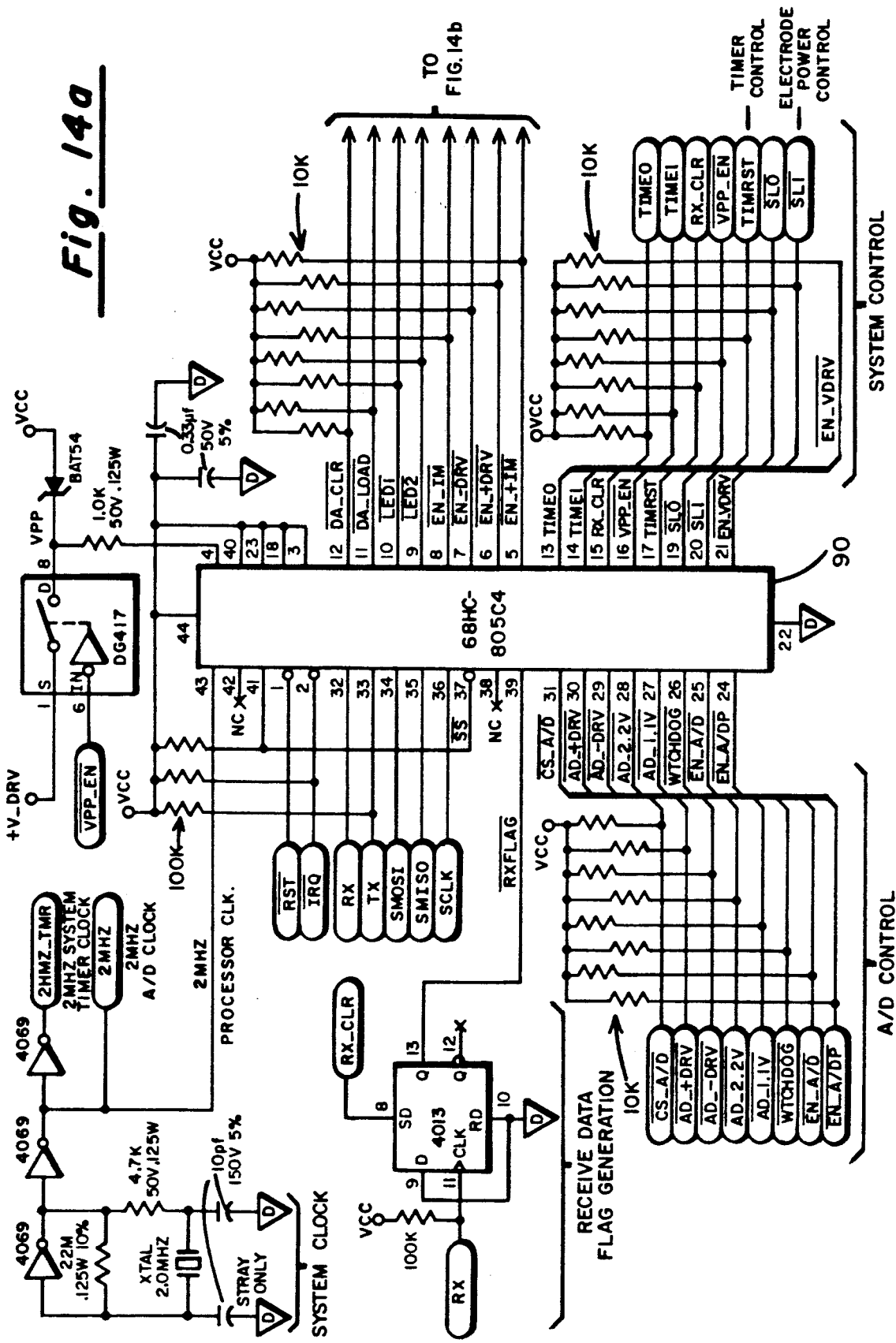
FIG. 14 is a schematic of the control processor for the stimulator portion with related circuitry.
Figure 14B:
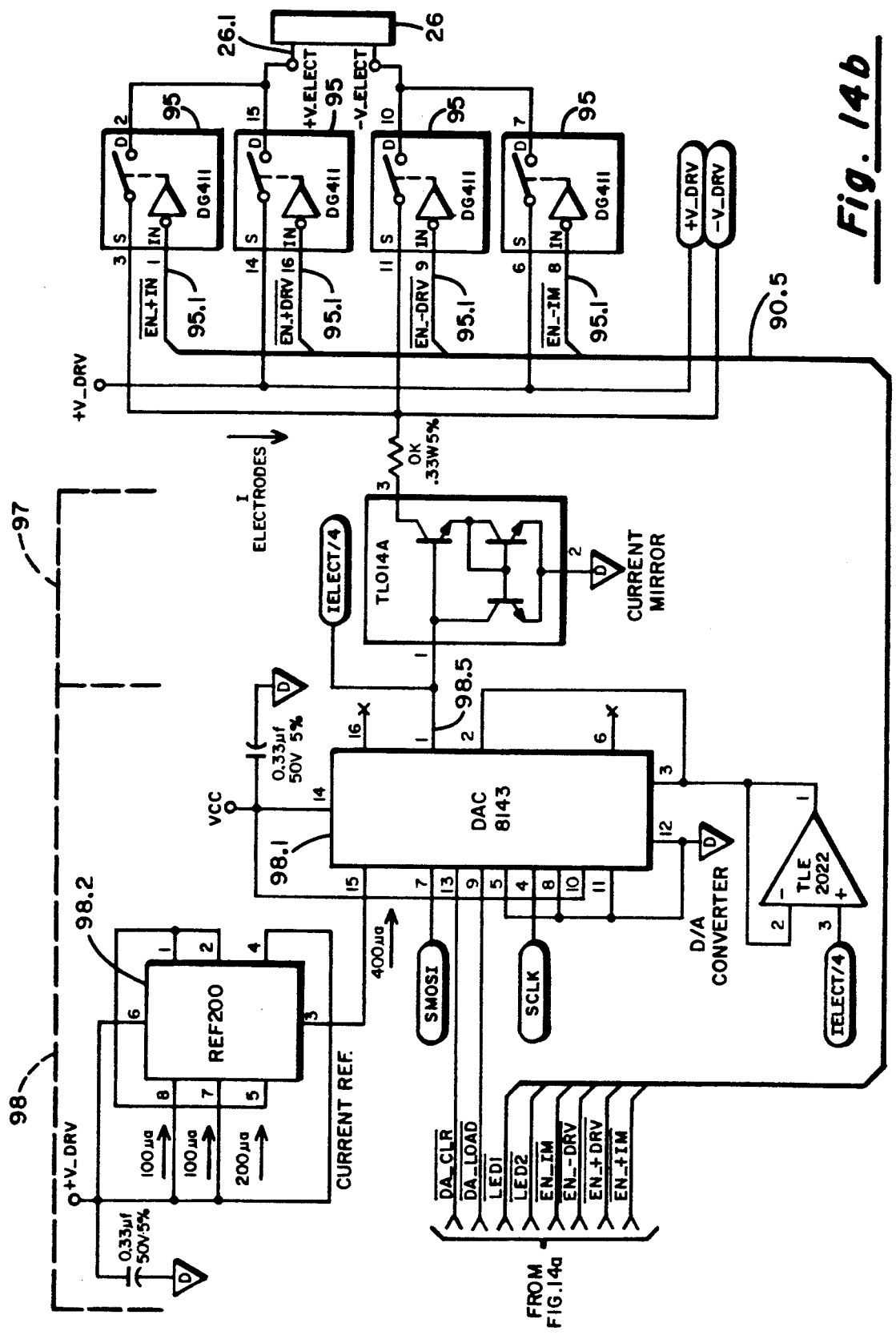

FIG. 14 shows the second control processor 90 and related circuitry. The second control processor 90 used in the preferred embodiment is a Motorola Semiconductor Inc. microcontroller No. 68HC805C4. The microcontroller has a system RAM, bootstrap ROM, EEPROM bank A, EEPROM bank B, a synchronous serial port, 24 general input/output pins and an interrupt controller. For specific information on the details of operation, programming, technical information, and specifications, see *Motorola Semiconductor Technical Data*, document No. AD1991R2, by Motorola, Inc., 1985, distributed by Motorola Literature Distribution.

FIG. 14 also shows the digital analog circuitry 98 comprised of the DAC8143 D/A converter 98.1, current reference integrated circuit 98.2, the current mirror 97, and the analog switches 95. The second control processor 90 is connected to the analog switches by way of electrode drive bus 90.5. The drive bus 90.5 connects to the operating terminals 95.1 of the analog switches 95. The output of the analog switches goes to the electrode cable 26.1 and the electrodes 26.

The current reference integrated circuit 98.2 supplies a maximum reference current to the converter. In the preferred embodiment 400 μA was used. The digital/analog converter 98.1 provides 100 output current levels at output 98.5. This output is presented to the current mirror 97 which provides a constant current source independent of the load with a gain of four. The control processor 90 directly controls the digital/analog converter 98.1.

Figure 15A:
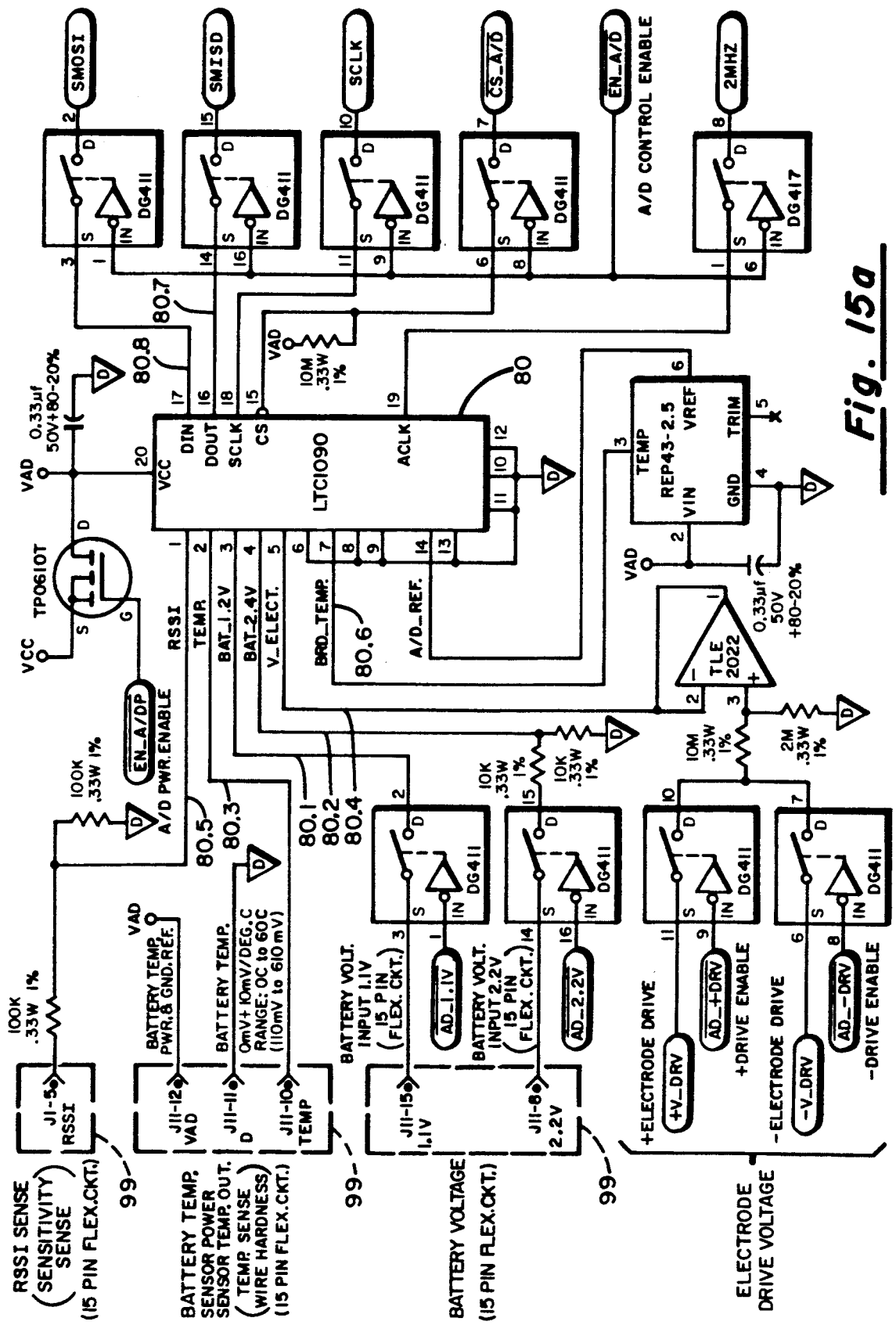

FIG. 15a shows an analog-to-digital converter integrated circuit 80, with inputs for battery voltage 80.1, 80.2, battery temperature 80.3, electrode drive voltage 80.4, receiver RF signal strength 80.5, and circuit board temperature 80.6. The output 80.7 of the converter 80 goes to the second control processor 90. The control processor 90 selects the specific parameter to input by way of "DIN" line 80.8. Notably, power to the converter 80 and the various inputs and outputs is switched under the control of the control processor 90. FIG. 15 shows the connections to the J11 connector 99.

Operation of specific circuits was discussed in reference to the figures. An overview of the operation of the stimulation and telemetry functions is as follows:

The electrical stimulus to the neural tissue is provided by the electrodes 26 attached to the stimulator portion 24. The potential to the electrodes 26 is provided through the analog switches 95. The second control processor 90 is appropriately programmed to control the analog switches to generate the stimuli with the specified parameters, i.e., monophasic, bi-phasic, direct current pulses, and with the specified amplitude and duration.

The parameters of the stimuli are changed by way of digitally encoded commands from the external controller portion 22 through the in-link telemetry system.

The in-link telemetry is accomplished by the first control processor 50 being programmed to encode commands and operate the modulator 42 to amplitude shift key the RF signal generated by RF synthesizers 45. The modulated RF signal goes to the first primary tuned circuit 31 which includes the first antenna coil 30. The first antenna coil 30 and second antenna coil 32 couple when in proximity to each other transferring the RF energy to tuned secondary circuit 33 of the stimulator portion 24. The envelope demodulator 82 and threshold detector 84 detect and shape the encoded signal by way of the rectifier, RC circuitry, and transfers the signal to the second control processor 90.

The second control processor 90 in the stimulator portion 24 is programmed to receive and decode the commands and controls the analog-to-digital converter 98.1 and the analog switches 95 to alter the stimuli parameters as commanded.

The first control processor 50 in the external controller portion 22 also is programmed to send commands requesting data on the battery voltage, battery temperature, circuit board temperature, electrode voltage, and the stimuli parameters. The second control processor 90 is programmed to enable the analog-to-digital converter 80 and the appropriate sensors to receive data on the requested conditions. The second control processor then encodes the data and operates the out-link telemetry to transmit the data to the external controller portion.

Out-link telemetry transmission is accomplished by the second control processor 90 switching the MOSFETS 86.1 and 86.2 ON and OFF in accordance with encoded data when the first and second antenna coils are coupled. The switch short circuits the tuned secondary circuit 33 and reflects back RF energy to the first antenna coil 30.

The external controller portion 22 receives the encoded out-link telemetry signal, and detects and demodulates the signal by way of the receiver circuitry 34. The first control processor 50 then decodes the data and stores the data in the system static RAM 55 and/or enables the LCD display circuitry 64 to display the data.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A nerve regeneration device of the type comprising an external controller portion and an implantable stimulator portion, the stimulator portion to provide electrical stimulus to nerve tissue;

the external controller comprising:
 a first antenna coil;
 a radio frequency transmitter connected to the antenna coil, the transmitter generating electromagnetic radiation at a selected transmission frequency; whereby the antenna coil radiates the electromagnetic radiation as a signal;
 a first receiver means connected to the first antenna coil to detect electromagnetic radiation reflected back to the first antenna coil, the receiver having means for generating a signal corresponding to the reflected electromagnetic radiation;
 a control processor connected to the receiver means, the control processor having means for receiving and responding to said signal;

the stimulator portion comprising:
 a second antenna coil that couples with the first antenna coil and absorbs a portion of the electromagnetic radiation;
 a sensing means for detecting a specified condition of the stimulator portion, the sensing means providing a condition indicating signal which varies as a function of the condition;

a reflecting means for reflecting a portion of the electromagnetic radiation as a signal back to the first antenna coil;

a switching means for activating and deactivating said reflecting means;

a second control processor connected to the switching means and to the sensing means; the control processor having means for operating the switching means in accordance with the condition indicating signal, whereby the reflected electromagnetic radiation forms an encoded signal corresponding to the specified condition.

2. The device of claim 1, wherein the signal produced by the first receiving means corresponds to the encoded signal.

3. The device of claim 2, wherein the control processor further comprises means for converting the signal from the first receiver means into a signal corresponding to the condition indicating signal, and wherein the external controller portion further comprises a display means, the display means connected to the first control processor the display means having means for responding to the signal from the first control processor for indicating the condition of the stimulator portion.

4. The device of claim 3, further comprising a full-wave bridge rectifier circuit connected to the tuned circuit whereby the rectifier circuit has a direct current voltage output and said output is connected to the rechargeable battery means, and wherein the transmitter and antenna coils are sized so that the direct current voltage output is sufficient to recharge the battery means.

5. The device of claim 4, wherein the stimulator portion further comprises a second receiving means connected to the second control processor, and wherein the radio frequency transmitter of the external controller portion comprises a modulator, said modulator connected to the first control processor, the first control processor having means for generating commands to the stimulator portion and to operate the modulator whereby the electromagnetic radiation radiated by the first antenna coil is modulated in accordance with said commands, the second receiving means having means for receiving said modulated electromagnetic radiation and means for conveying a signal corresponding to said commands to the second control processor, and wherein the second control processor includes means for responding to said commands.

6. The device of claim 1, wherein the reflecting means comprising a capacitor electrically connected to the second antenna coil forming a tuned circuit and a means for short circuiting said tuned circuit whereby said short circuiting effects the reflection of the electromagnetic radiation as a signal from the second antenna coil to the first antenna coil.

7. The device of claim 1, wherein the stimulator further comprises a battery means for providing power for the stimulator portion and said battery means is rechargeable.

8. A nerve regeneration device of the type comprising an external controller portion and an implantable stimulator portion that provides electrical stimulus to nerve tissue;

the external controller comprising:
a first antenna coil;
a radio frequency transmitter, the transmitter having means for generating a carrier wave, the transmitter including a means for modulating said carrier wave, the radio frequency transmitter connected to the first antenna coil whereby the antenna coil radiates the modulated carrier wave; and a first control processor which includes a means for encoding commands to produce an encoded signal to be sent to the stimulator portion, the first control processor connected to the modulating means of the radio frequency transmitter for modulating the carrier wave as a function of the encoded signal; and the stimulator portion comprising:
a second antenna coil;
a capacitor electrically connected to the antenna coil forming a tuned circuit whereby a coupling effect is created between first antenna coil and the second antenna coil when they are in proximity to each other, and whereby the modulating carrier wave is received by the second antenna coil;

a sensing means for detecting a condition of the stimulator portion, the sensing means providing a condition indicating signal which varies as a function of the condition;

a switching means connected to the tuned circuit, the switching means for short circuiting the tuned circuit whereby the carrier wave is reflected back to the first antenna coil;

a receiver means connected to the second antenna coil, the receiver means having means for receiving the modulated carrier wave and for generating an encoded signal corresponding to the encoded signal produced by the first control processor;

a second control processor connected to the receiver means for receiving and decoding the encoded commands from the external controller portion and for responding to said commands; the control processor further comprising an operating means connected to the switching means for short circuiting the tuned circuit corresponding to the condition indicating signal to be communicated to the external controller portion;

a rechargeable battery means for providing power for the stimulator portion; and a means for converting radio frequency power absorbed by the second antenna to recharge the battery means.

9. The device of claim 8, wherein the controller portion further comprises a first receiver means connected to the first antenna coil for detecting the carrier wave reflected back to the first antenna coil, the receiver means generating a signal corresponding to the reflected carrier wave.

10. The device of claim 9, wherein the means for converting the radio frequency power absorbed by the second antenna coil is comprised of a full wave bridge rectifier electrically connected to the tuned circuit.

11. The device of claim 10, wherein the condition is the battery temperature.

12. The device of claim 11, wherein the stimulator portion further comprises a second sensing means for monitoring battery voltage and generating a status indicating signal, said means connected to the control processor.

13. The device of claim 11, wherein the stimulator portion further comprising a plurality of electrodes to provide the electrical stimuli, and whereby electrodes have a voltage across them during stimulation and the stimulator portion further comprises a sensing means for monitoring said voltage and generating a third status indicating signal, said means connected to the control processor.

14. The device of claim 13, further comprising a sensing means for monitoring electrical current through said electrodes and for generating a condition indicating signal corresponding to said current, said means connected to the control processor.

15. The device of claim 14, wherein the carrier wave has a frequency between 1.5 and 2.5 MHz.

16. The device of claim 15, wherein the switching means is comprised of a metal-oxide-semiconductor field-effect transistor.

17. The device of claim 16, wherein the second control processor further comprises a storage means for retaining the commands from the external control portion.

18. The device of claim 17, wherein the stimulator portion further comprises switching means connected to the electrodes for controlling a parameter of the electrical stimuli, said means controlled by the second control processor.

19. The device of claim 18, wherein the electrical stimuli have a polarity and the parameter controlled by the switching means is the polarity of the electrical stimuli.

20. The device of claim 18, wherein the electrical stimuli have an amplitude and the switching means is for controlling said amplitude.

21. The device of claim 18, wherein the electrical stimuli have a frequency and the switching means is for controlling said frequency.

22. The device of claim 18, wherein the electrical stimuli have a pulse width and the analog switching means is for controlling said pulse width.

* * * * *

UNITED STATES PATENT AND TRADEMARK OFFICE
CERTIFICATE OF CORRECTION

PATENT NO. : 5,314,457

DATED : May 24, 1994

INVENTOR(S) : Dean C. Jeutter and Mark S. Geisler

It is certified that error appears in the above-identified patent and that said Letters Patent is hereby corrected as shown below:

On the title page, Item
(54), delete "REGENERATIVE ELECTRICAL" and substitute
--REGENERATIVE ELECTRICAL STIMULATOR--.

Signed and Sealed this

Twenty-seventh Day of September, 1994

Attest:

BRUCE LEHMAN

Attesting Officer

Commissioner of Patents and Trademarks